US010900068B2

(12) United States Patent
Rodesch et al.

(10) Patent No.: US 10,900,068 B2
(45) Date of Patent: *Jan. 26, 2021

(54) METHODS AND SYSTEMS FOR SOLUTION BASED SEQUENCE ENRICHMENT

(71) Applicant: Roche Sequencing Solutions, Inc., Pleasanton, CA (US)

(72) Inventors: Matthew Rodesch, McFarland, WI (US); Thomas Albert, Danville, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/706,133

(22) Filed: Sep. 15, 2017

(65) Prior Publication Data
US 2018/0030521 A1 Feb. 1, 2018

Related U.S. Application Data

(63) Continuation of application No. 13/239,585, filed on Sep. 22, 2011, now Pat. No. 9,790,543, which is a continuation of application No. 12/194,574, filed on Aug. 20, 2008, now abandoned.

(30) Foreign Application Priority Data

Oct. 23, 2007 (EP) ..................................... 07020660

(51) Int. Cl.
C12Q 1/68 (2018.01)
C12Q 1/6813 (2018.01)
C12Q 1/6844 (2018.01)
C12Q 1/6806 (2018.01)
C12N 15/10 (2006.01)

(52) U.S. Cl.
CPC ......... *C12Q 1/6813* (2013.01); *C12Q 1/6806* (2013.01); *C12Q 1/6844* (2013.01); *C12N 15/1006* (2013.01)

(58) Field of Classification Search
CPC ................ C12Q 1/6813; C12Q 1/6806; C12Q 2537/159; C12N 15/1006
See application file for complete search history.

(56) References Cited

U.S. PATENT DOCUMENTS

| | | |
|---|---|---|
| 5,143,854 A | 9/1992 | Pirrung et al. |
| 5,202,231 A | 4/1993 | Drmanac et al. |
| 5,437,976 A | 8/1995 | Utermohlen et al. |
| 5,445,934 A | 8/1995 | Fodor et al. |
| 5,527,681 A | 6/1996 | Holmes et al. |
| 5,547,839 A | 8/1996 | Dower et al. |
| 5,631,734 A | 5/1997 | Stern et al. |
| 5,800,992 A | 9/1998 | Fodor et al. |
| 5,837,832 A | 11/1998 | Chee et al. |
| 6,013,440 A * | 1/2000 | Lipshutz ............... C12Q 1/6806 435/5 |
| 6,103,463 A | 8/2000 | Chetverin et al. |
| 6,280,950 B1 | 8/2001 | Lipshutz et al. |
| 6,375,903 B1 | 4/2002 | Cerrina et al. |
| 6,440,677 B2 | 8/2002 | Lipshutz et al. |
| 6,569,621 B1 | 5/2003 | Cremer et al. |
| 6,828,104 B2 | 12/2004 | Lipshutz et al. |
| 7,037,659 B2 | 5/2006 | Cerrina et al. |
| 7,083,975 B2 | 8/2006 | Green et al. |
| 7,157,229 B2 | 1/2007 | Cerrina et al. |
| 7,534,561 B2 | 5/2009 | Sana et al. |
| 7,604,996 B1 | 10/2009 | Stuelpnagel et al. |
| 7,851,158 B2 | 12/2010 | McKernan et al. |
| 7,867,703 B2 | 1/2011 | Sampson et al. |
| 7,901,886 B2 | 3/2011 | Staehler et al. |
| 8,383,338 B2 | 2/2013 | Kitzman |
| 9,790,543 B2 | 10/2017 | Rodesch et al. |
| 2002/0132244 A1 | 9/2002 | Li-Sucholeiki |
| 2002/0137043 A1 | 9/2002 | Patil et al. |
| 2003/0108900 A1* | 6/2003 | Oliphant ............... C12Q 1/6834 435/6.12 |
| 2003/0148273 A1 | 8/2003 | Dong et al. |
| 2004/0132056 A1 | 7/2004 | Su et al. |
| 2004/0259146 A1 | 12/2004 | Friend et al. |
| 2005/0100911 A1 | 5/2005 | Patil et al. |
| 2005/0142577 A1* | 6/2005 | Jones ................... C12Q 1/6809 435/6.12 |
| 2005/0252209 A1 | 12/2005 | Albert et al. |
| 2006/0046251 A1 | 3/2006 | Sampson et al. |

(Continued)

FOREIGN PATENT DOCUMENTS

EP 0328829 A2 8/1989
EP 0392546 A2 10/1990

(Continued)

OTHER PUBLICATIONS

Albert, T J et al , "Direct selection of human genomic loci by microarray hybridization", 2007, Nature Methods, vol. 4, No. 11, pp. 903-905.

Morgulis, A E et al , "WindowMasker window-based masker for sequenced genomes", 2006, Bioinformatics, vol. 22, No. 2, pp. 134-141.

Soares, M B et al , "Construction and characterization of a normalized cDNA library", 1994, Proc Natl Acad Sci , vol. 91, No. 20, pp. 9228-9232.

Nuwaysir, E F et al , "Gene expression analysis using oligonucleotide arrays produced by maskless photolithography", 2002, Genome Research, vol. 12, pp. 1749-1755.

(Continued)

*Primary Examiner* — David C Thomas
(74) *Attorney, Agent, or Firm* — Eric Grant Lee; Daniel Agnew

(57) ABSTRACT

The present invention provides methods and systems for the capture and enrichment of target nucleic acids and analysis of the enriched target nucleic acids. In particular, the present invention provides for the enrichment of targeted sequences in a solution based format.

Figure 1:
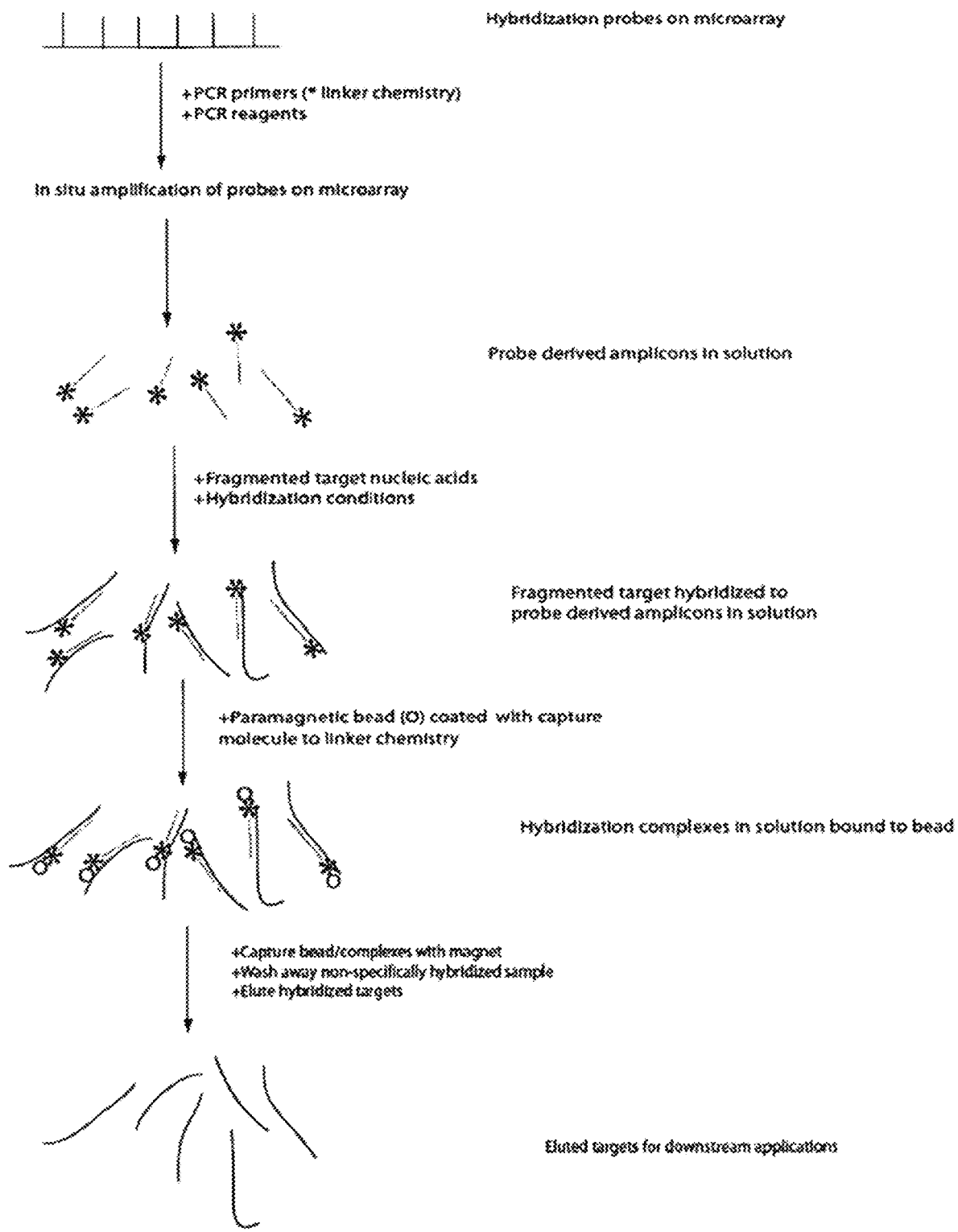

18 Claims, 2 Drawing Sheets
Specification includes a Sequence Listing.

(56) References Cited

U.S. PATENT DOCUMENTS

| | | | |
|---|---|---|---|
| 2006/0068415 A1 | 3/2006 | Jones et al. | |
| 2006/0183132 A1* | 8/2006 | Fu | C12Q 1/6806 |
| | | | 435/6.12 |
| 2007/0087349 A1 | 4/2007 | Staehler et al. | |
| 2007/0141604 A1 | 6/2007 | Gormley et al. | |
| 2007/0196843 A1 | 8/2007 | Green et al. | |
| 2008/0194414 A1* | 8/2008 | Albert | C12N 15/1093 |
| | | | 506/1 |
| 2009/0209436 A1* | 8/2009 | Larman | B01J 19/0046 |
| | | | 506/9 |
| 2009/0221438 A1 | 9/2009 | Kitzman et al. | |
| 2010/0331204 A1 | 12/2010 | Jeddaloh et al. | |
| 2012/0046175 A1 | 2/2012 | Rodesch et al. | |

FOREIGN PATENT DOCUMENTS

| | | |
|---|---|---|
| EP | 0552290 | 7/1993 |
| EP | 1184466 A2 | 3/2002 |
| WO | 1989010977 | 11/1989 |
| WO | 1990003382 | 5/1990 |
| WO | 1992007091 A1 | 4/1992 |
| WO | 1993017126 | 9/1993 |
| WO | 1997010365 | 3/1997 |
| WO | 9923256 A1 | 5/1999 |
| WO | 200026415 | 11/2000 |
| WO | 2005082098 A2 | 9/2005 |
| WO | 2005084277 A2 | 9/2005 |
| WO | 2006002281 A1 | 1/2006 |
| WO | 2007057652 | 5/2007 |
| WO | 2008115185 A3 | 9/2008 |
| WO | 2009053039 | 4/2009 |

OTHER PUBLICATIONS

Matsuzaki, H et al., "Parallel Genotyping of Over 10,000 SNPs Using a One-Primer Assay on a High-Density Oligonucleotide Array", 2004, Genome Research, vol. 14, No. 3, pp. 414-425.

Garraway, L et al., "Array-based approaches to cancer genome analysis", 2005, Drug Discovery Today, vol. 2, pp. 171-177.

Calhoun, E et al., "Identifying Allelic Loss and Homozygous Deletions in Pancreatic Cancer without Matched Normals Using High-Density Single-Nucleotide Polymorphism Arrays", 2006, Cancer Research, vol. 66, No. 16, pp. 7920-7928.

Oliphant et al., BeadArray™ Technology. Enabling an Accurate, Cost-Effective Approach to High-Throughput Genotyping, BioTechniques, Jun. 2002, S56-S61, 32.

Bashiardes et al, Direct genomic selection, Nature Methods, Jan. 2005, pp. 63-69, vol. 2, No. 1.

Kai et al, Purification of single stranded DNA from asymmetric PCR product using the SMART system, Biotechnology Techniques, Dec. 1998, pp. 935-939, vol. 12, No. 12.

Kijas, J.M.H., et al., Enrichment of Microsatellites from the Citrus Genome Using Biotinylated Oligonucleotide Sequences Bound to Streptavidin-Coated Magnetic Particles, BioTechniques, 1994, pp. 187-193, 16(4).

Muscatelli et al, Isolation and characterization of a MAGE gene family in the Xp21.3 region, Proceedings of the National Academy of Sciences USA, May 1995, pp. 4987-4991, vol. 92.

Porreca et al, Multiplex amplification of large sets of human exons, Nature Methods, Nov. 2007, p. 935, vol. 4, No. 11.

Bertone, Paul, et al., "Design optimization methods for genomic DNA filing arrays," Genome Research, vol. 16, pp. 271-281, published 2006 ("Bertone").

Gunderson, Kevin, et al., "Mutation Detection by Litigation to Complete n-mer DNA Arrays," Genome Research, vol. 8, pp. 1142-1153, published 1998.

Hardenbol, Paul, et al., "Highly multiplexed molecular inversion probe genotyping: Over 10,000 targeted SNPs genotyped in a single tube assay," Genome Research, vol. 15, pp. 269-275, published 2005 ("Hardenbol").

Hodges et al., Nature Genetics, Genome-wide in situ exon capture for selective resequencing, published on line, Nov. 4, 2001.

Lipshutz, Robert J., et al., "High density synthetic oligonucleotide arrays," Nature Genetics Supplement, vol. 21, pp. 20-24, published Jan. 1999 ("Lipshutz Article").

Livesey et al "An analysis of the gene expression program of mammalian neural progenitor cells" PNAS vol. 101(5) 1374-1379 (Feb. 2004).

Lovett et al, Direct Selection: A Method for the isolation of cDNAs encoded by large genomic regions, Proceedings of the National Academy of Sciences, Nov. 1991, pp. 9628-9632, vol. 88.

Noonan et al 2006, supporting supplemental material for "Sequencing and Analysis of Neanderthal Genomic DNA", Science, vol. 314, pp. 1113-1118, published Nov. 17, 2006 ("Noonan Supp.").

Noonan, James P., et al., "Sequencing and Analysis of Neanderthal Genomic DNA," Science, vol. 314, pp. 1113-1118, published Nov. 17, 2006 ("Noonan").

Welcher, Andrew A., et al., "Selective enrichment of specific DNA, cDNA and RNA sequences using biotinylated proves, avidin and copper-chelate agarose," Nucleic Acids Research, IRL Press Ltd., Oxford, England, vol. 14, pp. 10027-10044, published Nov. 24, 1986 ("Welcher").

Petition for Inter Partes Review of U.S. Pat. No. 9,790,543 Under 35 U.S.C. 311-319 and 37 C.F.R. 42.100 et seq. (Sep. 24, 2018).

Porreca et al., (Multiplex amplification of large sets of human exons, 2007, Nature Methods, vol. 4, pp. 931-936, published online Oct. 21, 2007), plus Supplementary Materials, 17 pages total.

Bashiardes, et al. (Direct genomic selection, 2005, Nature Methods, vol. 2, pp. 63-69).

Kai et al. (Purification of single stranded DNA from assymetric PCR product using the SMART system, 1998, Biotechnology Techniques, vol. 12, pp. 935-939).

Muscatelli et al. (Isolation and characterization of a MAGE gene family in the Xp21,3 region, 1995, PNAS, vol. 92, pp. 4987-4991).

* cited by examiner

SEQUENCE LISTING

```
<160> NUMBER OF SEQ ID NOS: 29

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligonucleotide 1

<400> SEQUENCE: 1
ctcgagaatt ctggatcctc                                              20

<210> SEQ ID NO 2
<211> LENGTH: 22
<212> TYPE: DNA
<213> ORGANISM: Artificial Sequence
<220> FEATURE:
<223> OTHER INFORMATION: Synthetic Oligonucleotide 2

<400> SEQUENCE: 2
gaggatccag aattctcgag tt                                           22

<210> SEQ ID NO 3
<211> LENGTH: 22
<212> TYPE: DNA
<213> ORGANISM: Artificial Sequence
<220> FEATURE:
```

<223> OTHER INFORMATION: Region 1 Forward Primer

<400> SEQUENCE: 3
ctaccacggc cctttcataa ag                                            22

<210> SEQ ID NO 4
<211> LENGTH: 21
<212> TYPE: DNA
<213> ORGANISM: Artificial Sequence
<220> FEATURE:
<223> OTHER INFORMATION: Region 1 Reverse Primer

<400> SEQUENCE: 4
agggagcatt ccaggagaga a                                             21

<210> SEQ ID NO 5
<211> LENGTH: 20
<212> TYPE: DNA
<213> ORGANISM: Artificial Sequence
<220> FEATURE:
<223> OTHER INFORMATION: Region 2 Forward Primer

<400> SEQUENCE: 5
ggccagggct gtgtacagtt                                               20

<210> SEQ ID NO 6
<211> LENGTH: 26
<212> TYPE: DNA
<213> ORGANISM: Artificial Sequence
<220> FEATURE:
<223> OTHER INFORMATION: Region 2 Reverse Primer

<400> SEQUENCE: 6
ccgtatagaa gagaagactc aatgga                                        26

<210> SEQ ID NO 7
<211> LENGTH: 19
<212> TYPE: DNA
<213> ORGANISM: Artificial Sequence
<220> FEATURE:
<223> OTHER INFORMATION: Region 3 Forward Primer

<400> SEQUENCE: 7
tgccccacgg taacagatg                                                19

<210> SEQ ID NO 8
<211> LENGTH: 20
<212> TYPE: DNA
<213> ORGANISM: Artificial Sequence
<220> FEATURE:
<223> OTHER INFORMATION: Region 3 Reverse Primer

<400> SEQUENCE: 8
ccacgctggt gatgaagatg                                               20

<210> SEQ ID NO 9
<211> LENGTH: 17
<212> TYPE: DNA
<213> ORGANISM: Artificial Sequence
<220> FEATURE:
<223> OTHER INFORMATION: Region 4 Forward Primer

<400> SEQUENCE: 9
tgcagggcct gggttct                                                  17

-continued

```
<210> SEQ ID NO 10
<211> LENGTH: 18
<212> TYPE: DNA
<213> ORGANISM: Artificial Sequence
<220> FEATURE:
<223> OTHER INFORMATION: Region 4 Reverse Primer

<400> SEQUENCE: 10
gcggagggag agctcctt                                                 18

<210> SEQ ID NO 11
<211> LENGTH: 27
<212> TYPE: DNA
<213> ORGANISM: Artificial Sequence
<220> FEATURE:
<223> OTHER INFORMATION: Region 5 Forward Primer

<400> SEQUENCE: 11
gtctctttct ctctcttgtc cagtttt                                       27

<210> SEQ ID NO 12
<211> LENGTH: 21
<212> TYPE: DNA
<213> ORGANISM: Artificial Sequence
<220> FEATURE:
<223> OTHER INFORMATION: Region 5 Reverse Primer

<400> SEQUENCE: 12
cactgtcttc tcccggacat g                                             21

<210> SEQ ID NO 13
<211> LENGTH: 21
<212> TYPE: DNA
<213> ORGANISM: Artificial Sequence
<220> FEATURE:
<223> OTHER INFORMATION: Reverse 6 Forward Primer

<400> SEQUENCE: 13
agccagaaga tggaggaagc t                                             21

<210> SEQ ID NO 14
<211> LENGTH: 19
<212> TYPE: DNA
<213> ORGANISM: Artificial Sequence
<220> FEATURE:
<223> OTHER INFORMATION: Reverse 6 Reverse Primer

<400> SEQUENCE: 14
ttaaagcgct tggcttgga                                                19

<210> SEQ ID NO 15
<211> LENGTH: 26
<212> TYPE: DNA
<213> ORGANISM: Artificial Sequence
<220> FEATURE:
<223> OTHER INFORMATION: Region 7 Forward Primer

<400> SEQUENCE: 15
tcttttgaga aggtataggt gtggaa                                        26

<210> SEQ ID NO 16
<211> LENGTH: 17
<212> TYPE: DNA
<213> ORGANISM: Artificial Sequence
<220> FEATURE:
<223> OTHER INFORMATION: Region 7 Reverse Primer
```

-continued

<400> SEQUENCE: 16
caggcccagg ccacact                                                    17

<210> SEQ ID NO 17
<211> LENGTH: 19
<212> TYPE: DNA
<213> ORGANISM: Artificial Sequence
<220> FEATURE:
<223> OTHER INFORMATION: Region 8 Forward Primer

<400> SEQUENCE: 17
cgaggcctgc acagtatgc                                                  19

<210> SEQ ID NO 18
<211> LENGTH: 20
<212> TYPE: DNA
<213> ORGANISM: Artificial Sequence
<220> FEATURE:
<223> OTHER INFORMATION: Region 8 Reverse Primer

<400> SEQUENCE: 18
gcgggctcag cttcttagtg                                                 20

<210> SEQ ID NO 19
<211> LENGTH: 15
<212> TYPE: DNA
<213> ORGANISM: Artificial Sequence
<220> FEATURE:
<223> OTHER INFORMATION: PCR Primer 1a

<400> SEQUENCE: 19
tgccggagtc agcgt                                                      15

<210> SEQ ID NO 20
<211> LENGTH: 15
<212> TYPE: DNA
<213> ORGANISM: Artificial Sequence
<220> FEATURE:
<223> OTHER INFORMATION: Biotinylated PCR Primer 1b

<400> SEQUENCE: 20
agtcagagtc gccac                                                      15

<210> SEQ ID NO 21
<211> LENGTH: 18
<212> TYPE: DNA
<213> ORGANISM: Artificial Sequence
<220> FEATURE:
<223> OTHER INFORMATION: Synthetic oligonucleotide linker

<400> SEQUENCE: 21
ctcgagaatt ctggatcc                                                   18

<210> SEQ ID NO 22
<211> LENGTH: 23
<212> TYPE: DNA
<213> ORGANISM: Artificial Sequence
<220> FEATURE:
<223> OTHER INFORMATION: qPCR 0210 Forward Primer

<400> SEQUENCE: 22
gaccctctta ccttggcatt ctc                                             23

<210> SEQ ID NO 23
<211> LENGTH: 20

<212> TYPE: DNA
<213> ORGANISM: Artificial Sequence
<220> FEATURE:
<223> OTHER INFORMATION: qPCR 0210 Reverse Primer

<400> SEQUENCE: 23
gctggtaccc attggcaact                                           20

<210> SEQ ID NO 24
<211> LENGTH: 26
<212> TYPE: DNA
<213> ORGANISM: Artificial Sequence
<220> FEATURE:
<223> OTHER INFORMATION: qPCR 0271 Forward Primer

<400> SEQUENCE: 24
ggagtgagtg gttttcttc attttt                                     26

<210> SEQ ID NO 25
<211> LENGTH: 20
<212> TYPE: DNA
<213> ORGANISM: Artificial Sequence
<220> FEATURE:
<223> OTHER INFORMATION: qPCR 0271 Reverse Primer

<400> SEQUENCE: 25
gcgccacaaa gagacattca                                           20

<210> SEQ ID NO 26
<211> LENGTH: 22
<212> TYPE: DNA
<213> ORGANISM: Artificial Sequence
<220> FEATURE:
<223> OTHER INFORMATION: qPCR 0266 Forward Primer

<400> SEQUENCE: 26
aaggccatac ttgggtgaac tg                                        22

<210> SEQ ID NO 27
<211> LENGTH: 20
<212> TYPE: DNA
<213> ORGANISM: Artificial Sequence
<220> FEATURE:
<223> OTHER INFORMATION: qPCR 0266 Reverse Primer

<400> SEQUENCE: 27
gctctgattg gtggcttcgt                                           20

<210> SEQ ID NO 28
<211> LENGTH: 21
<212> TYPE: DNA
<213> ORGANISM: Artificial Sequence
<220> FEATURE:
<223> OTHER INFORMATION: qPCR 0283 Forward Primer

<400> SEQUENCE: 28
tgcttgcagg tgtctctcag a                                         21

<210> SEQ ID NO 29
<211> LENGTH: 27
<212> TYPE: DNA
<213> ORGANISM: Artificial Sequence
<220> FEATURE:
<223> OTHER INFORMATION: qPCR 0283 Reverse Primer

```
<400> SEQUENCE: 29
cagtgagata tttggtacca tggtgta                                                        27
```

METHODS AND SYSTEMS FOR SOLUTION BASED SEQUENCE ENRICHMENT

CROSS-REFERENCE TO RELATED APPLICATIONS

The present application is a continuation of U.S. patent application Ser. No. 13/239,585, filed Sep. 22, 2011, which is a continuation U.S. patent application Ser. No. 12/194,574, filed Aug. 20, 2008, which claims priority to European Patent Application Serial Number 07020660.2 filed Oct. 23, 2007, each of which is incorporated herein by reference in its entirety.

FIELD OF THE INVENTION

The present invention provides methods and systems for the capture and enrichment of target nucleic acids and analysis of the enriched target nucleic acids. In particular, the present invention provides for the enrichment of targeted sequences in a solution based format.

BACKGROUND OF THE INVENTION

The advent of nucleic acid microarray technology makes it possible to build an array of millions of nucleic acid sequences in a very small area, for example on a microscope slide (e.g., U.S. Pat. Nos. 6,375,903 and 5,143,854). Initially, such arrays were created by spotting pre-synthesized DNA sequences onto slides. However, the construction of maskless array synthesizers (MAS) as described in U.S. Pat. No. 6,375,903 now allows for the in situ synthesis of oligonucleotide sequences directly on the slide itself.

Using a MAS instrument, the selection of oligonucleotide sequences to be constructed on the microarray is under software control such that it is now possible to create individually customized arrays based on the particular needs of an investigator. In general, MAS-based oligonucleotide micro array synthesis technology allows for the parallel synthesis of millions of unique oligonucleotide features in a very small area of a standard microscope slide. With the availability of the entire genomes of hundreds of organisms, for which a reference sequence has generally been deposited into a public database, microarrays have been used to perform sequence analysis on nucleic acids isolated from a myriad of organisms.

Nucleic acid microarray technology has been applied to many areas of research and diagnostics, such as gene expression and discovery, mutation detection, allelic and evolutionary sequence comparison, genome mapping, drug discovery, and more. Many applications require searching for genetic variants and mutations across the entire human genome that underlies human diseases. In the case of complex diseases, these searches generally result in a single nucleotide polymorphism (SNP) or set of SNPs associated with diseases and/or disease risk. Identifying such SNPs has proved to be an arduous and frequently fruitless task because resequencing large regions of genomic DNA, usually greater than 100 kilo bases (Kb), from affected individuals or tissue samples is required to find a single base change or to identify all sequence variants. Other applications involve the identification of gains and losses of chromosomal sequences which may also be associated with cancer, such as lymphoma (Martinez-Climent J A et al., 2003, Blood 101:3109-3117), gastric cancer (Weiss M Metal., 2004, Cell. Oncol. 26:307-317), breast cancer (Callagy G et al., 2005, J. Path. 205: 388-396) and prostate cancer (Paris, P L et al., 2004, Hum. Mol. Gen. 13:1303-1313). As such, microarray technology is a tremendously useful tool for scientific investigators and clinicians in their understanding of diseases and therapeutic regimen efficacy in treating diseases.

The genome is typically too complex to be studied as a whole, and techniques must be used to reduce the complexity of the genome. To address this problem, one solution is to reduce certain types of abundant sequences from a DNA sample, as found in U.S. Pat. No. 6,013,440. Alternatives employ methods and compositions for enriching genomic sequences as described, for example, in Albert et al. (2007, Nat. Meth., 4:903-5), Okou et al. (2007, Nat. Meth. 4:907-9), Olson M. (2007, Nat. Meth. 4:891-892), Hodges et al. (2007, Nat. Genet. 39:1522-1527) and as found in U.S. patent application Ser. Nos. 11/638,004, 11/970,949, and 61/032,594. Albert et al. disclose an alternative that is both cost-effective and rapid in effectively reducing the complexity of a genomic sample in a user defined way to allow for further processing and analysis. Lovett et al. (1991, Proc. Natl. Acad. Sci. 88:9628-9632) also describes a method for genomic selection using a bacterial artificial chromosomes. However, existing methods are limited by, for example, their ease of use and inflexibility of materials and methods.

Prior art microarray technology, be it enrichment technology or otherwise, is typically a substrate associated technology with inherent variability, such as microarray slides, chips, and the like. Variability can take on many forms, for example variability in background, probe/hybridization kinetics, glass source, and the like. Variability plays a big part in experimental interpretation and can make or break an experiment.

As such, what are needed are methods, systems and compositions to provide enrichment of targeted sequences in a format that other than a typical substrate type of micro array format. The advent of new micro array formats will provide additional tools for researchers and clinicians in advancing their knowledge of diseases and disease states.

SUMMARY OF THE INVENTION

The present invention provides methods and systems for the capture and enrichment of target nucleic acids and analysis of the enriched target nucleic acids. In particular, the present invention provides for the enrichment of targeted sequences in a solution based format. Methods and systems of the present invention are useful in aiding investigators and clinicians in identifying, studying and following treatment regimens associated with disease and disease states.

The present invention is summarized as a novel method for reducing the complexity of a large nucleic acid sample, such as a genomic sample, cDNA library or mRNA to facilitate further processing and genetic analysis. Embodiments of the present invention comprise (preselected) immobilized nucleic acid probes to capture target nucleic acid sequences from, for example, a genomic sample by hybridizing the sample to probes, or probe derived amplicons, on a solid support or in solution. The captured target nucleic acids are preferably washed and eluted off of the probes. The eluted genomic sequences are more amenable to detailed genetic analysis than a sample that has not been subjected to the methods described herein. The present invention provides methods and systems for the capture and enrichment of target nucleic acids and analysis of the enriched target nucleic acids. In some embodiments, the present invention provides for the enrichment of targeted sequences in a solution based format. In some embodiments, the present invention provides methods and systems for solution based capture and enrichment of target nucleic acids (e.g., genomic DNA, RNA, cDNA, mRNA, etc.).

The disclosed methods provide a cost-effective, flexible and efficient approach for reducing the complexity of a genomic sample. Genomic samples are used herein for descriptive purposes, but it is understood that other non-genomic samples could be subjected to the same procedures. The methods and systems described herein provide for enrichment of target sequences in a solution based approach thereby providing an alternative to microarray substrate based methods for use in research and therapeutics associated with disease and disease states such as cancers (Durkin et al., 2008, Proc. Natl. Acad. Sci. 105:246-251; Natrajan et al., 2007, Genes, Chr. And Cancer 46:607-615; Kim et al., 2006, Cell125:1269-1281; Stallings et al., 2006 Can. Res. 66:3673-3680), genetic disorders (Balciuniene et al., Am. J. Hum. Genet. In press), mental diseases (Walsh et al., 2008, Science 320:539-543; Roohi et al., 2008, J. Med. Genet. Epub 18 Mar. 2008; Sharp et al., 2008, Nat. Genet. 40:322-328; Kumar et al., 2008, Hum. Mol. Genet. 17:628-638;) and evolutionary and basic research (Lee et al., 2008, Hum. Mol. Gen. 17:1127-1136; Jones et al., 2007, BMC Genomics 8:402; Egan et al., 2007, Nat. Genet. 39:1384-1389; Levy et al., 2007, PLoS Biol. 5:e254; Ballif et al., 2007, Nat. Genet. 39:1071-1073; Scherer et al., 2007, Nat. Genet. S7-S15; Feuk et al., 2006, Nat. Rev. Genet. 7:85-97), to name a few.

In some embodiments of the present invention, solution based capture methods comprise probe derived amplicons wherein said probes for amplification are affixed to a solid support. The solid support comprises support-immobilized nucleic acid probes to capture specific nucleic acid sequences (e.g., target nucleic acids) from, for example, a genomic sample. Probe amplification provides probe amplicons in solution which are hybridized to target sequences. Following hybridization of probe amplicons to target sequences, target nucleic acid sequences present in the sample are enriched by capturing (e.g., via linker chemistry such as biotin, digoxigenin, etc.) and washing the probes and eluting the hybridized target nucleic acids from the captured probes (FIG. 1). The target nucleic acid sequence(s), may be further amplified using, for example, nonspecific ligation-mediated PCR (LM-PCR), resulting in an amplified pool of PCR products of reduced complexity compared to the original target sample.

In some embodiments, hybridization between the probes and target nucleic acids is performed under preferably stringent conditions sufficient to support hybridization between the solution based probe amplicons, wherein said probes comprise linker chemistry and complementary regions of the target nucleic acid sample to provide probe/target hybridization complexes. The complexes are subsequently captured via the linker chemistry and washed under conditions sufficient to remove non-specifically bound nucleic acids and the hybridized target nucleic acid sequences are eluted from the captured probe/target complexes.

The present invention provides methods of isolating and reducing the genetic complexity of a plurality of nucleic acid molecules, the method comprising the steps of exposing fragmented, denatured nucleic acid molecules of said population to multiple, different oligonucleotide probes that are bound on a solid support under hybridizing conditions to capture nucleic acid molecules that specifically hybridize to said probes, or exposing fragmented, denatured nucleic acid molecules of said population to multiple, different oligonucleotide probes under hybridizing conditions followed by binding the complexes of hybridized molecules to a solid support to capture nucleic acid molecules that specifically hybridize to said probes, wherein in both cases said fragmented, denatured nucleic acid molecules have an average size of about 100 to about 1000 nucleotide residues, preferably about 250 to about 800 nucleotide residues and most preferably about 400 to about 600 nucleotide residues, separating unbound and nonspecifically hybridized nucleic acids from the captured molecules, eluting the captured molecules, and optionally repeating the aforementioned processes for at least one further cycle with the eluted captured molecules.

In some embodiments, the multiple, different oligonucleotide probes comprise a chemical group or linker chemistry, for example a binding moiety such as biotin, digoxigenin, etc., which is able to bind to a solid support. The solid support for binding comprises the corresponding capture chemistry, for example streptavidin for biotin and anti-digoxigenin antibody for digoxigenin. A skilled artisan will recognize that the present invention is not limited by the linker chemistry used and alternative linker chemistries are equally amenable to methods and systems of the present invention.

In embodiments of the present invention, the population or plurality of target nucleic acid molecules preferably contains the whole genome or at least one chromosome of an organism or at least one nucleic acid molecule with at least about 100 kb. In particular, the size(s) of the nucleic acid molecule(s) is/are at least about 200 kb, at least about 500 kb, at least about 1 Mb, at least about 2 Mb or at least about 5 Mb, especially a size between about 100 kb and about 5 Mb, between about 200 kb and about 5 Mb, between about 500 kb and about 5 Mb, between about 1 Mb and about 2 Mb or between about 2 Mb and about 5 Mb.

In some embodiments, the target nucleic acid molecules are selected from an animal, a plant or a microorganism, in preferred embodiments the organism is a human. If only limited samples of nucleic acids (e.g. of the human genome) are available, the nucleic acids may be amplified, for example by whole genome amplification, prior to practicing the methods of the present invention. Prior amplification may be necessary for performing the inventive method(s), for example, for forensic purposes (e.g. in forensic medicine for genetic identity purposes).

In some embodiments, the population of target nucleic acid molecules is a population of genomic DNA molecules. In such embodiments, probes are selected from a plurality of sequences that, for example, define a plurality of exons, introns or regulatory sequences from a plurality of genetic loci, a plurality of probes that define the complete sequence of at least one single genetic locus, said locus having a size of at least 100 kb, preferably at least 1 Mb, or at least one of the sizes as specified above, a plurality of probes that define single nucleotide polymorphisms (SNPs), or a plurality of probes that define an array, for example a tiling array designed to capture the complete sequence of at least one complete chromosome.

In some embodiments, the present invention comprises the step of ligating adaptor molecules to one or both, preferably both ends of the nucleic acid molecules prior to or after exposing fragmented nucleic samples to the probes for hybridization. In some embodiments, methods of the present invention further comprise the amplifying of the target nucleic acid molecules with at least one primer, said primer comprising a sequence which specifically hybridizes to the sequence of said adaptor molecule(s). In some embodiments, the amplified target nucleic acid sequences may be sequenced, hybridized to a resequencing or SNP-calling array and the sequence or genotypes may be further analyzed.

In some embodiments, the present invention provides an enrichment method for target nucleic acid sequences in a genomic sample, such as exons or variants, preferably SNP sites. This can be accomplished by synthesizing genomic probes specific for a region of the genome to capture complementary target nucleic acid sequences contained in a complex genomic sample.

In some embodiments, the present invention further comprises determining the nucleic acid sequence of the captured and eluted target molecules, in particular by means of performing sequencing by synthesis reactions. In some embodiments, the present invention is directed to a method for detecting coding region variation relative to a reference genome, in particular relative to a reference genome that comprises fragmented, denatured genomic nucleic acid molecules, the method as previously described further comprising determining the nucleic acid sequence of the captured and eluted target molecules, in particular by means of performing sequencing by synthesis reactions and comparing the determined sequence to a sequence in a database, in particular to a sequence in a database of polymorphisms in the reference genome to identify variants from the reference genome.

In some embodiments, the present invention is directed to a kit comprising compositions and reagents for performing a method according to the present invention. Such a kit may comprise, but is not limited to, a double stranded adaptor molecule, multiple, different oligonucleotide probes, a solid support for capturing said probes, wherein the probes are selected from a plurality of sequences that define a plurality of exons, introns or regulatory sequences from a plurality of genetic loci, a plurality of probes that define the complete sequence of at least one single genetic locus, said locus having a size of at least 100 kb, preferably at least 1 Mb, or at least one of the sizes as specified above, a plurality of probes that define sites known to contain SNPs, or a plurality of probes that define a tiling array designed to capture the complete sequence of at least one complete chromosome. In some embodiments, a kit comprises a plurality of beads or a microarray substrate (e.g., slide, chip, etc.). In some embodiments, a kit comprises two different double stranded adaptor molecules. A kit may further comprise at least one or more other components selected from DNA polymerase, T4 polynucleotide kinase, T4 DNA ligase, hybridization solution(s), wash solution(s), and/or elution solution(s).

In embodiments of the present invention, nucleic acid (pre-selected) capture probes are immobilized onto a solid support (e.g., slide, chip, bead, etc.) using any number of recognized methods (e.g., spotting, photolithography, in situ synthesis, etc.). In preferred embodiments, the probes are synthesized in situ by maskless array synthesis on a substrate and subsequently amplified by, for example, PCR resulting in probe derived amplicons in solution. In some embodiments, the probe sequences as synthesized comprise primer binding sites for amplification at one or both the 3' and 5' termini (e.g., at or near the ends) of the probes. In some embodiments, the sequence of the primer binding sites on the probes are the same at both the 3' and 5' prime ends or the probes, whereas in other embodiments the sequence of the primer binding sites is different at the 3' prime end then the sequence at the 5' prime end. In some embodiments, amplification primers for probe amplification further comprise a restriction endonuclease site, for example an MlyI site for easy removal of primer sequences from the final captured target, wherein one of the primers (e.g., forward or reverse primer) further comprises linker chemistry such as a binding moiety or sequence (e.g., biotin, digoxigenin, HIS tag, etc.) and are deposited onto the support with the immobilized probes along with reagents necessary for exponential PCR amplification (e.g., PCR procedures for exponential amplification of targets as known to a skilled artisan). PCR is performed thereby creating amplicons of probe capture sequences such that one of the strands comprises linker chemistry, such as a binding moiety or sequence. The amplicon containing solution is transferred to a vessel (e.g., tube, well of a 96 well plate, etc.) and, in some embodiments, purified from reaction components. An additional round of amplification is preferentially performed on the probe derived amplicons using asymmetric PCR, wherein the linker chemistry labeled primer is in abundance compared to the non-labeled primer to preferentially synthesize single stranded binding moiety/sequence labeled amplicons. The amplicons are purified away from reaction components and transferred to a vessel, denatured nucleic acid sample is added, and hybridization is allowed to occur.

Following hybridization, labeled amplicon/target nucleic acid complexes are captured. For example, when biotin is the binding moiety a streptavidin (SA) coated substrate such as SA coated beads (e.g., paramagnetic beads/particles) are used to capture the biotin labeled amplicon/target complex. The SA bound complex is washed and the hybridized target nucleic acids are eluted from the complex and utilized in downstream applications, such as sequencing applications.

In some embodiments, the present invention provides methods for isolating and reducing the complexity of a plurality of nucleic acid sequences comprising providing a solid support wherein said solid support comprises hybridization probes hybridizable to target nucleic acid sequences and providing a fragmented nucleic acid sample comprising target nucleic acid sequences, amplifying the hybridization probes wherein the amplification products comprise a binding moiety and wherein the amplification products are in solution, hybridizing the nucleic acid sample to the amplification products in solution under conditions such that hybridization between the amplification products and target nucleic acid sequences is allowed to occur, separating the hybridized target nucleic acid sequences/amplification product complexes from non-specifically hybridized nucleic acids by said binding moiety, and eluting the hybridized target nucleic acid sequences from the complex thereby isolation and reducing the complexity of a plurality of nucleic acid sequences. In some embodiments, the solid support is a micro array slide. In some embodiments, the target nucleic acid sample is fragmented genomic DNA with or without adaptor molecules at one or both ends of the fragments. In some embodiments, the hybridization probes comprise a restriction endonuclease site, for example a MlyI site. In some embodiments, probe amplification comprises exponential polymerase chain reaction, and may further comprise asymmetric non-exponential amplification. In some embodiments, the binding moiety is biotin and the capture substrate, such as a bead for example a paramagnetic particle, is coated with streptavidin for separation of the target nucleic acid/amplification product complex from non-specifically hybridized target nucleic acids. In some embodiments, the captured target nucleic acid/amplification product complexes are washed prior to elution of the bound target nucleic acids. In some embodiments, the eluted target nucleic acids are sequenced.

In some embodiments, the present invention provides methods for isolating and reducing the complexity of a plurality of nucleic acid sequences comprising providing a solid support wherein said solid support comprises hybridization probes hybridizable to target nucleic acid sequences and providing a fragmented nucleic acid sample comprising target nucleic acid sequences, amplifying the hybridization probes wherein the amplification products comprise a binding moiety and wherein the amplification products are in solution, hybridizing the nucleic acid sample to the amplification products in solution under conditions such that hybridization between the amplification products and target nucleic acid sequences is allowed to occur, separating the hybridized target nucleic acid sequences/amplification product complexes from non-specifically hybridized nucleic acids by said binding moiety, eluting the hybridized target nucleic acid sequences from the complex thereby isolation and reducing the complexity of a plurality of nucleic acid sequences, and sequencing the eluted target nucleic acid sequences. In some embodiments, the solid support is a microarray slide. In some embodiments, the target nucleic acid sample is fragmented genomic DNA with or without adaptor molecules at one or both ends of the fragments. In some embodiments, the hybridization probes comprise a restriction endonuclease site, for example a MlyI site. In some embodiments, probe amplification comprises exponential polymerase chain reaction, and may further comprise asymmetric non-exponential amplification. In some embodiments, the binding moiety is biotin and the capture substrate, such as a bead for example a paramagnetic particle, is coated with streptavidin for separation of the target nucleic acid/amplification product complex from non-specifically hybridized target nucleic acids. In some embodiments, the captured target nucleic acid/amplification product complexes are washed prior to elution of the bound target nucleic acids.

In some embodiments, the present invention provides a kit comprising hybridization probe sequences comprising a binding moiety and a restriction enzyme site wherein said probe sequences are designed to hybridize to one or more target nucleic acid sequences and wherein said probe sequences are in solution, a substrate comprising a binding partner for binding said binding moiety, and instruction for performing methods of the present invention. In some embodiments, a kit further comprises one or more solutions such as hybridization, washing, and elution solution(s). In some embodiments, a kit comprises a magnet. In some embodiments, a kit comprises one or more enzymes and corresponding reagents, buffers, and the like, for example a restriction enzyme such as MlyI and buffers/reagents for performing restriction enzyme reactions using MlyI.

Definitions

As used herein, the term "sample" is used in its broadest sense. In one sense, it is meant to include a specimen or culture obtained from any source, preferentially a biological source. Biological samples may be obtained from animals (including humans) and encompass fluids, solids, tissues, and gases. Biological samples include blood products, such as plasma, serum and the like. As such, a "sample of nucleic acids" or a "nucleic acid sample", a "target sample" comprises nucleic acids (e.g., DNA, RNA, cDNA, mRNA, tRNA, miRNA, etc.) from any source. In the present application, a nucleic acid sample preferably derives from a biological source, such as a human or non-human cell, tissue, and the like. The term "non-human" refers to all non-human animals and entities including, but are not limited to, vertebrates such as rodents, non-human primates, ovines, bovines, ruminants, lagomorphs, porcines, caprines, equines, canines, felines, ayes, etc. Non-human also includes invertebrates and prokaryotic organisms such as bacteria, plants, yeast, viruses, and the like. As such, a nucleic acid sample used in methods and systems of the present invention is a nucleic acid sample derived from any organism, either eukaryotic or prokaryotic.

As used herein, the term "hybridization" is used in reference to the pairing of complementary nucleic acids. Hybridization and the strength of hybridization (e.g., the strength of the association between the nucleic acids) is affected by such factors as the degree of complementary between the nucleic acids, stringency of the conditions involved, the melting temperature (Tm) of the formed hybrid, and the G:C ratio of the nucleic acids. While the invention is not limited to a particular set of hybridization conditions, stringent hybridization conditions are preferably employed. Stringent hybridization conditions are sequence dependent and differ with varying environmental parameters (e.g., salt concentrations, presence of organics, etc.). Generally, "stringent" conditions are selected to be about 50° C. to about 20° C. lower than the Tm for the specific nucleic acid sequence at a defined ionic strength and pH. Preferably, stringent conditions are about 5° C. to 10° C. lower than the thermal melting point for a specific nucleic acid bound to a complementary nucleic acid. The Tm is the temperature (under defined ionic strength and pH) at which 50% of a nucleic acid (e.g., target nucleic acid) hybridizes to a perfectly matched probe.

"Stringent conditions" or "high stringency conditions," for example, can be hybridization in 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 mg/ml), 0.1% SDS, and 10% dextran sulfate at 42° C., with washes at 42° C. in 0.2% SSC (sodium chloride/sodium citrate) and 50% formamide at 55° C., followed by a wash with 0.1×SSC containing EDTA at 55° C. By way of example, but not limitation, it is contemplated that buffers containing 35% formamide, 5×SSC, and 0.1% (w/v) sodium dodecyl sulfate (SDS) are suitable for hybridizing under moderately non-stringent conditions at 45° C. for 16-72 hours.

Furthermore, it is envisioned that the formamide concentration may be suitably adjusted between a range of 20-45% depending on the probe length and the level of stringency desired. Additional examples of hybridization conditions are provided in several sources, including Molecular Cloning: A Laboratory Manual, Eds. Sambrook et al., Cold Spring Harbour Press (incorporated herein by reference in its entirety).

Similarly, "stringent" wash conditions are ordinarily determined empirically for hybridization of a target to a probe, or in the present invention, a probe derived amplicon. The amplicon/target are hybridized (for example, under stringent hybridization conditions) and then washed with buffers containing successively lower concentrations of salts, or higher concentrations of detergents, or at increasing temperatures until the signal-to-noise ratio for specific to non-specific hybridization is high enough to facilitate detection of specific hybridization. Stringent temperature conditions will usually include temperatures in excess of about 30° C., more usually in excess of about 37° C., and occasionally in excess of about 45° C. Stringent salt conditions will ordinarily be less than about 1000 mM, usually less than about 500 mM, more usually less than about 150 mM (Wetmur et al., 1966, J. Mol. Biol., 31:349-370; Wetmur, 1991, Critical Reviews in Biochemistry and Molecular Biology, 26:227-259, incorporated by reference herein in their entireties).

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (e.g., in the presence of nucleotides and an inducing agent such as DNA polymerase and at a suitable temperature and pH). The primer is preferably single stranded for maximum efficiency in amplification. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (e.g., a sequence of nucleotides), whether occurring naturally as in a purified restriction digest or produced synthetically, recombinantly or by PCR amplification, that is capable of hybridizing to at least a portion of another oligonucleotide of interest, for example target nucleic acid sequences. A probe may be single-stranded or double-stranded. Probes are useful in the detection, identification and isolation of particular gene sequences.

As used herein, the term "target nucleic acid molecules" and "target nucleic acid sequences" are used interchangeably and refer to molecules or sequences from a target genomic region to be studied. The pre-selected probes determine the range of targeted nucleic acid molecules. Thus, the "target" is sought to be sorted out from other nucleic acid sequences. A "segment" is defined as a region of nucleic acid within the target sequence, as is a "fragment" or a "portion" of a nucleic acid sequence.

As used herein, the term "isolate" when used in relation to a nucleic acid, as in "isolating a nucleic acid" refers to a nucleic acid sequence that is identified and separated from at least one component or contaminant with which it is ordinarily associated in its natural source. Isolated nucleic acid is in a form or setting that is different from that in which it is found in nature. In contrast, non-isolated nucleic acids as nucleic acids such as DNA and RNA found in the state they exist in nature. The isolated nucleic acid, oligonucleotide, or polynucleotide may be present in single-stranded or double-stranded form.

FIGURES

FIG. 1 exemplifies an embodiment of the present invention; a generalized flow diagram of an enrichment process wherein said enrichment methods are used to isolate and enrich for a plurality of nucleic acid sequences in an aqueous solution. Hybridization probes, affixed to a microarray substrate, are amplified in situ to produce probe derived amplicons in solution the amplicons of which comprise a binding moiety. Fragmented nucleic acids (e.g. labeled with a detection moiety) are hybridized in solution to the labeled probe amplicons, the complexes being subsequently captured (e.g., by paramagnetic capture particles). The captured and immobilized hybridized complexes are washed and the specifically bound targets are eluted from the bound immobilized probe amplicons. The eluted (e.g., isolated and enriched) target sequences are applied to downstream applications, such as sequencing.

Figure 2:
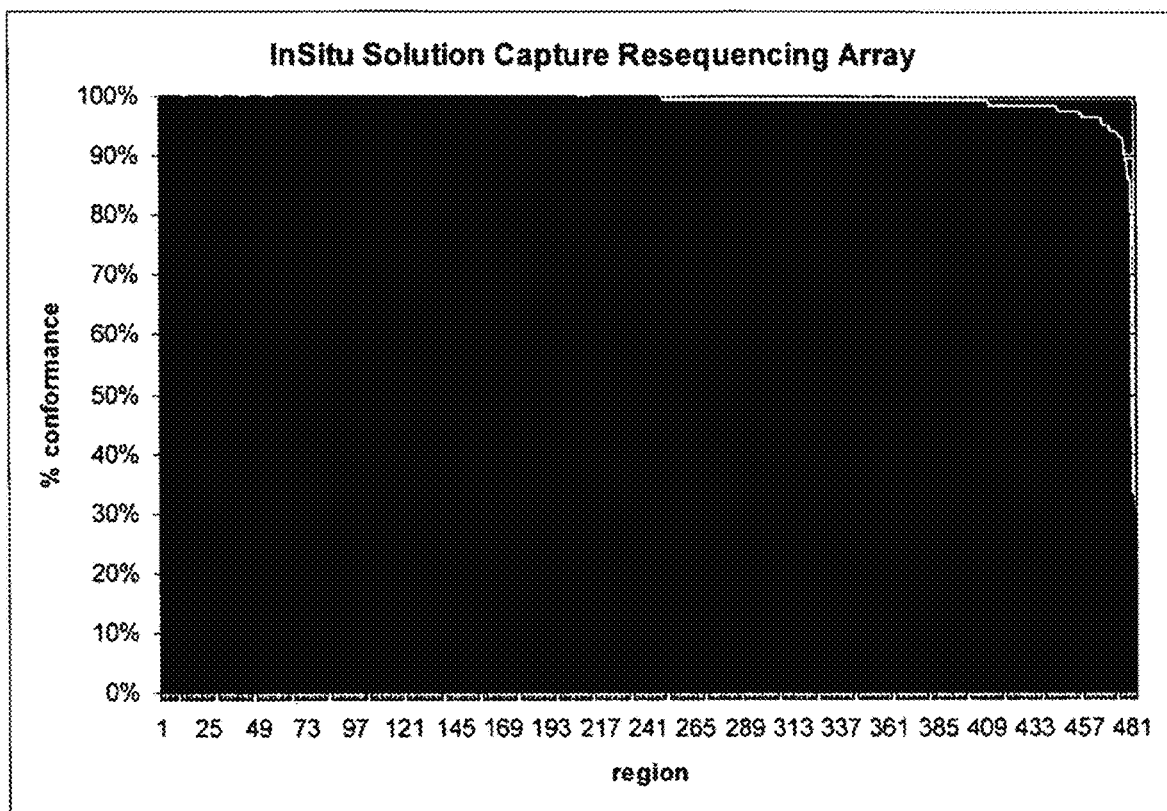

FIG. 2 demonstrates resequencing conformance using the solution capture methods of the present invention. The resequencing assay is comprised of a subset of the targeted captured regions. The x-axis represents an arbitrary set of regions from the larger target region, which serves as a representation of the targeted capture region as a whole. They-axis represents the percent sequence conformance with known target sequences.

DETAILED DESCRIPTION OF THE INVENTION

The present invention broadly relates to cost-effective, flexible and rapid solution based methods and systems for isolating a plurality of nucleic acid sequences and reducing nucleic acid sample complexity to enrich for target nucleic acids of interest and to facilitate further processing and analysis, such as sequencing, resequencing and SNP calling. The captured target nucleic acid sequences, which are of a more defined, less complex genomic population are more amenable to detailed genetic analysis, for example genetic analysis of disease and disease states (e.g., cancers, genetic mutations, genetic diseases, etc). The present invention provides methods and systems useful, for example, in searching for genetic variants and mutations such a single nucleotide polymorphisms (SNPs), sets of SNPs, genomic insertions, deletions, etc. that underlie human diseases.

In embodiments of the present invention, a sample containing denatured (e.g., single-stranded) nucleic acid molecules, preferably genomic nucleic acid molecules, which can be fragmented molecules, is exposed under hybridizing conditions to a plurality of oligonucleotide probes, wherein the plurality of oligonucleotide probes or amplicons derived from said probes are in solution, to capture from the sample nucleic acid molecules target nucleic acid sequences and separating non-hybridizing regions of the genome or any other sample nucleic acids from the hybridized target sequences, wherein said separating comprises capturing via a binding moiety (e.g., associated with the probe or probe derived amplicon) the hybridization complexes that are in solution and washing the bound complexes thereby separating the hybridized target sequences from the non-specific non-target hybridized sequences (FIG. 1).

The present invention provides methods and systems for isolating a plurality of nucleic acid sequences and reducing the complexity of a large nucleic acid sample, such as a genomic DNA or RNA sample, cDNA library or mRNA library to facilitate further processing and genetic analysis. In some embodiments of the present invention, methods and systems comprise in situ amplification of (pre-selected) immobilized nucleic acid probes wherein the probe derived amplicons comprise a binding moiety. The labeled amplicons capture, in solution, target nucleic acid sequences from a sample by hybridizing the sample to the amplicons in solution based methods. The labeled amplicon/target nucleic acid hybrid complex is captured via the binding moiety, preferably washed and the target nucleic acid eluted. The eluted genomic sequences are more amenable to detailed genetic analysis than a genomic sample that has not been subjected to this enrichment procedure. Accordingly, the disclosed methods provide a cost-effective, flexible and efficient approach for reducing the complexity of a genomic sample. Throughout the remainder of the description, genomic samples are used for descriptive purposes, but it is understood that other non-genomic samples could be subjected to the same procedures.

In some embodiments, the invention provides a method of isolating a plurality of nucleic acid sequences and reducing the complexity of a nucleic acid sample by hybridizing the sample against nucleic acid probe amplicons in solution under preferably stringent conditions sufficient to support hybridization between the probe amplicons and complementary regions of the nucleic acid sample. The probe amplicon/target nucleic acid complexes are washed under conditions sufficient to remove non-specifically bound nucleic acids. The hybridized target nucleic acid sequences are eluted from the probe derived amplicons and may optionally be further amplified (e.g., by LM-PCR), for example for downstream applications such as resequencing.

The present invention provides a method for isolating a plurality of nucleic acid sequences and reducing the genetic complexity of a population of nucleic acid molecules, the method comprising the steps of exposing fragmented, denatured nucleic acid molecules of a target population to multiple, different oligonucleotide probe derived amplicons wherein the amplicons are in solution and wherein the amplicons further comprise a binding moiety, under hybridizing conditions to capture nucleic acid molecules that specifically hybridize to the probe amplicons, binding or capturing the complexes of hybridized molecules by binding the binding moiety found on the probe amplicon to its binding partner (e.g., biotin/SA, digoxigenin/antidigoxigenin, 6HIS/nickel, etc.), wherein the fragmented, denatured nucleic acid molecules have an average size of about 100 to about 1000 nucleotide residues, preferably about 250 to about 800 nucleotide residues and most preferably about 400 to about 600 nucleotide residues, separating unbound and non-specifically hybridized nucleic acids from the bound probe amplicons, eluting the hybridized target molecules from the amplicons, and optionally sequencing the target molecules.

As such, embodiments of the present invention provide solution based methods and systems for isolating a plurality of nucleic acid sequences and reducing the genetic complexity of a population of nucleic acid molecules. Methods and systems of the present invention comprise exposing fragmented, denatured nucleic acid sample sequences, which may or may not comprise one or more ligation adaptors at one or both ends of the fragmented nucleic acid sample prior to denaturation, to multiple, different hybridization probe amplicons in solution wherein said amplicons are derived from pre-designed multiple, different hybridization probes wherein said amplicons comprise a binding moiety or sequence and optionally a restriction endonuclease (RE) site, under hybridization conditions sufficient to hybridize the denatured nucleic acid target sequences to the probe derived amplicons (e.g., in solution), wherein the fragmented, denatured nucleic acid sequences have an average size of about 100 to about 1000 nucleotide residues, preferably about 250 to about 800 nucleotide residues and most preferably about 400 to about 600 nucleotide residues, separating unbound and non-specifically hybridized nucleic acids from the probe derived amplicons by binding the amplicon/target complexes via the binding moiety and washing the bound complexes, eluting the target nucleic acid sequences from the bound complex wherein the target sequenced demonstrate reduced genetic complexity relative to the original sample and optionally repeating the hybridization, wash and elution steps using the initial eluted enriched target nucleic acid sequences to further enrich for target nucleic acid sequences.

In embodiments of the present invention, probes for capture of target nucleic acids are immobilized on a substrate by a variety of methods. In one embodiment, probes can be spotted onto slides (e.g., U.S. Pat. Nos. 6,375,903 and 5,143,854). In preferred embodiments, probes are synthesized in situ on a substrate by using maskless array synthesizers (MAS) as described in U.S. Pat. Nos. 6,375,903, 7,037,659, 7,083,975, 7,157,229 that allows for the in situ synthesis of oligonucleotide sequences directly on the slide for subsequent in situ polymerase chain reaction (PCR) amplification.

In some embodiments, a solid support is a population of beads or particles. The capture probes are initially synthesized on a microarray slide using a maskless array synthesizer, amplified, released or cleaved off according to standard methods, optionally amplified and immobilized on said population of beads. The beads may be packed, for example, into a column so that a target sample is loaded and passed through the column and hybridization of probe/target sample takes place in the column, followed by washing and elution of target sample sequences for reducing genetic complexity. In some embodiments, a column has fluid inlet and outlet ports. In some embodiments, in order to enhance hybridization kinetics hybridization takes place in an aqueous solution comprising the beads with the immobilized multiple probes in suspension in an aqueous environment.

In some embodiments, nucleic acid probes for target molecules are synthesized on a solid support, released from the solid support as a pool of probes and amplified. The amplified pool of released probed are covalently or non-covalently immobilized onto a support (e.g., glass, metal, ceramic, polymeric beads, paramagnetic particles, etc.). The probes are designed for convenient release from the solid support by, for example, providing at or near the support-proximal probe termini an acid or alkali-labile nucleic acid sequence that releases the probes under conditions of low or high pH, respectively. The art is familiar with methods for immobilizing nucleic acids onto supports, for example by incorporating a biotinylated nucleotide into the probes and coating a support with streptavidin such that the coated support attracts and immobilizes the probes in the pool. The sample or samples pass across the probe containing support (e.g., slide, column, etc.) under hybridizing conditions such that target nucleic acid molecules that hybridize to the immobilized support can be eluted for subsequent analysis or other use.

In embodiments of the present invention, the initial hybridization probes designed for subsequent amplification for use in solution based capture methods as described herein are printed or deposited on a solid support such as a microarray slide, chip, microwell, column, tube, beads or particles. The substrates may be, for example, glass, metal, ceramic, polymeric beads, etc. In preferred embodiments, the solid support is a microarray (e.g., glass slide), wherein the probes are synthesized on the microarray using a maskless array synthesizer. The lengths of the multiple oligonucleotide probes may vary and are dependent on the experimental design and limited only by the possibility to synthesize such probes. In preferred embodiments, the average length of the population of multiple probes prior to in situ amplification is about 20 to about 100 nucleotides, preferably about 40 to about 85 nucleotides, in particular about 45 to about 75 nucleotides. The immobilized hybridization probes are subsequently utilized as the templates for in situ PCR amplification and optionally asymmetric PCR amplification thereby providing probe derived amplicons for solution based hybridization and enrichment of target nucleic acid molecules from a complex sample.

In embodiments of the present invention, hybridization probes correspond in sequence to at least one region of a genome and can be provided on a solid support in parallel using, for example, maskless array synthesis (MAS) technology. Alternatively, probes can be obtained serially using a standard DNA synthesizer and then applied to the solid support or can be obtained from an organism and then immobilized on the solid support. In embodiments of the present invention, it is contemplated that hybridization probes, regardless of the method of synthesis, comprise amplification primer sequences for use in amplification techniques. In embodiments of the present invention, amplification primer sequences incorporated into hybridization probe sequences further comprise restriction endonuclease (RE) sequences. In embodiments of the present invention, hybridization probes as found on a microarray substrate are amplified in situ using primers complementary to the primer sequences wherein one or both of the primers further comprise linker chemistry, such as a binding moiety (e.g., biotin, digoxigenin, etc.) and such that the hybridization probe derived PCR amplicons are in solution.

The solution comprising the probe derived amplicons is transferred to, for example, a tube, well, or other vessel and maintained in solution. It is contemplated that one or more additional rounds of amplification to boost the production of the amplicon strand that comprises the binding moiety, for example by asymmetric PCR, is additionally performed. A nucleic acid sample, preferably fragmented and denatured to yield fragmented single stranded target sequences, is added to the amplicons in solution and hybridization is allowed to occur between the probe derived amplicons and the fragmented single stranded target nucleic acid sample. After hybridization, nucleic acids that do not hybridize, or that hybridize non-specifically, are separated from the amplicon/target complex by capturing the amplicon/target complex via the binding moiety and washing the amplicon/target complex. For example, if the binding moiety is biotin, a streptavidin coated substrate is used to capture the complex. The bound complex is washed, for example with one or more washing solutions. The remaining nucleic acids (e.g., specifically bound to the amplicons) are eluted from the complex, for example, by using water or an elution buffer (e.g., comprising TRIS buffer and/or EDTA) to yield an eluate enriched for the target nucleic acid sequences.

Microarray based oligonucleotides provided for amplification in solution based capture methods and systems as described herein are designed to target a region or regions of a genome. The length of individual probes is typically between 50 and 200 bases. These probes may be either designed to be overlapping probes, meaning that the starting nucleotides of adjacent probes are separated in the genome by less than the length of a probe, or non-overlapping probes, where the distance between adjacent probes are greater than the length of a probe. The distance between adjacent probes is generally overlapping, with spacing between the starting nucleotide of two probes varying between 1 and 100 bases. The distance is varied to cause some genomic regions to be targeted by a larger number of probes than others. This variation is used, for example, to modulate the capture efficiency of individual genomic regions, normalizing capture. Probes can be tested for uniqueness in the genome. In preferred embodiments of the present invention, to avoid non-specific binding of genomic elements to probe derived amplicons, highly repetitive elements of the genome are excluded from selection probe designs using a method that utilizes a strategy similar to the Window Masker program developed by, for example, Morgolis (2006, Bioinformatics 15:134-141, incorporated herein by reference in its entirety) to identify these regions and exclude them from probe design.

The nature and performance of the designed probes for amplification for solution based capture methods of the present invention can be varied to advantageously normalize or adjust the distribution of the target molecules captured and enriched in accord with the methods of the present invention. A goal of such normalization is to deliver one expressed gene per read (e.g., Soares, et al., 1994, Proc. Natl. Acad. Sci. 91:9228-9232). Normalization is applied, for example, to populations of cDNA molecules before library construction since generally the distribution of molecules in the population reflects the different expression levels of expressed genes from which the cDNA molecule populations are produced. For example, the number of sequencing reactions required to effectively analyze each target region is reduced by normalizing the number of copies of each target sequence in the enriched population such that across the set of probes the capture performance of distinct probes is normalized, on the basis of a combination of fitness and other probe attributes.

Fitness, characterized by a capture metric, is ascertained either informatically or empirically. In one approach, the ability of the target molecules to bind is adjusted by providing so-called isothermal (Tm-balanced) oligonucleotide probes, as described in U.S. Patent Publication No. 2005/10282209, that enable uniform probe performance, eliminate hybridization artifacts and/or bias and provide higher quality output. Probe lengths are adjusted (typically, about 20 to about 100 nucleotides, preferably about 40 to about 85 nucleotides, in particular about 45 to about 75 nucleotides, but optionally also more than 100 nucleotides until about 250 nucleotides) to equalize the melting temperature (e.g. Tm=76° C., typically about 55° C. to about 76° C., in particular about 72° C. to about 76° C.) across the entire set of probes prior to amplification. Thus, probes are optimized to perform equivalently at a given stringency in the genomic regions of interest, including AT- and GC-rich regions. The skilled artisan will appreciate that probe length, melting temperature and sequence can be coordinately adjusted for any given probe derived amplicon to arrive at a desired hybridization performance for the probe amplicon. For example, the melting temperature (Tm) of the probe derived amplicon can be calculated using the formula: $Tm=Sx(Gn+Cn)+lx(An+Tn)$, where n is the number of each specific base (A, T, G or C) present on the probe amplicon.

Capture performance can also be normalized by ascertaining the capture fitness of probe amplicons in the probe set, and then adjusting the quantity of individual probes on the solid support for amplification purposes accordingly. For example, if probe amplicons derived from a first probe is anticipated to capture twenty times as much nucleic acid as a second set of probe derived amplicons, then the capture performance of both probe amplicon sets can be equalized by providing twenty times as many copies of the second probe from amplification purposes, for example by increasing by twenty-fold the number of microarray probes displaying the second probe prior to amplification.

In other embodiments, an additional strategy for normalizing capture of target nucleic acids is to subject the eluted target molecules to a second round of solution based hybridization against the probe derived amplicons under less stringent conditions than were used for the first hybridization round. Apart from the substantial enrichment in the first hybridization that reduces complexity relative to the original genomic nucleic acid, the second hybridization can be conducted under hybridization conditions that saturate all capture probes. Presuming that substantially equal amounts of the probe derived amplicons are provided in solution, saturation of the amplicons will ensure that substantially equal amounts of each target are eluted after the second hybridization and washing.

In embodiments of the present invention, amplification primers utilized for in situ amplification of the hybridization probes for subsequent solution based capture and enrichment methods and systems described herein, comprise linker chemistry such as binding moieties. Binding moieties comprise any moiety that is attached or incorporated into the 5' end of an amplification primer useful in subsequent capture of the probe amplicon/target nucleic acid hybridization complex. A binding moiety is any sequence that is engineered into 5' of a primer sequence, such as a 6 histidine (6HIS) sequence that is capturable. For example, a primer that comprises a 6HIS sequence is captureable by nickel, for example in a tube, microwell, or purification column that is coated with nickel or contains nickel coated beads, particles, etc. wherein the beads are packed into a column and a sample is loaded and passed through the column for capture of the complex for reducing complexity (e.g., and subsequent target elution). Another example of a binding moiety useful in embodiments of the present invention includes a hapten, for example digoxigenin that is, for example, attached to the 5' end of an amplification primer. Digoxigenin is capturable by use of an antibody to digoxigenin, for example a substrate that is coated or contains an anti-digoxigenin antibody.

In preferred embodiments, an amplification primer used in methods and systems of the present invention contains a biotin moiety attached to the 5' end of the primer and subsequent probe derived amplicons. Biotin is capturable by streptavidin (SA), as such the biotin labeled amplicon can be captured on a substrate or column that is coated or contains SA. In preferred embodiments, streptavidin is coated onto paramagnetic particles that can be in turn captured magnetically for easy washing and elution of the target enriched nucleic acids. The present invention is not limited by the kind of linker chemistry used, and a skilled artisan will know of other options that are equally amendable to methods and systems of the present invention.

In embodiments of the present invention, the methods and systems comprise determining nucleic acid sequence information about at least one region of nucleic acid(s), in particular genomic nucleic acid(s), (the whole genome or at least one whole or partial chromosome) in a sample, the method comprising the steps of performing the methods as previously described followed by determining the nucleic acid sequence of the captured molecules, in particular by performing sequencing by synthesis reactions.

In embodiments of the present invention, target nucleic acids are typically deoxyribonucleic acids or ribonucleic acids, and include products synthesized in vitro by converting one nucleic acid molecule type (e.g., DNA, RNA and cDNA) to another as well as synthetic molecules containing nucleotide analogues. Denatured genomic DNA molecules are in particular molecules that are shorter than naturally occurring genomic nucleic acid molecules. A skilled person can produce molecules of random- or non-random size from larger molecules by chemical, physical or enzymatic fragmentation or cleavage using well known protocols. For example, chemical fragmentation can employ ferrous metals (e.g., Fe-EDTA), physical methods can include sonication, hydrodynamic force or nebulization (e.g., see European patent application EP 0 552 290) and enzymatic protocols can employ nucleases such as micrococcal nuclease (Mnase) or exo-nucleases (such as Exo1 or Bal31) or restriction endonucleases.

The present invention is not limited to the method in which fragments are generated and any method useful in fragmenting nucleic acids is contemplated. In embodiments of the present invention, fragments in a size range compatible with the post-enrichment technology in which the enriched fragments are preferred. For example, embodiments of the present invention contemplate nucleic acid fragment sizes in the range of between about 100 and about 1000 nucleotide residues or base pairs, or between about 250 and about 800 nucleotide residues or base pairs, or about 400 to about 600 nucleotide residues or base pairs, in particular about 500 nucleotide residues or base pairs.

The population of nucleic acid molecules which may comprise the target nucleic acid sequences preferably contains the whole genome or at least one chromosome of an organism or at least one nucleic acid molecule with at least about 100 kb. In particular, the size(s) of the nucleic acid molecule(s) is/are at least about 200 kb, at least about 500 kb, at least about 1 Mb, at least about 2 Mb or at least about 5 Mb, especially a size between about 100 kb and about 5 Mb, between about 200 kb and about 5 Mb, between about 500 kb and about 5 Mb, between about 1 Mb and about 2 Mb or between about 2 Mb and about 5 Mb. In some embodiments, the nucleic acid molecules are genomic DNA, while in other embodiments the nucleic acid molecules are cDNA, or RNA species (e.g., tRNA, mRNA, miRNA).

In embodiments of the present invention, the nucleic acid molecules which may or may not comprise the target nucleic acid sequences may be selected from an animal, a plant or a microorganism, in particular embodiments the nucleic acid molecules are from a primate, preferably a human. In some embodiments, if limited samples of nucleic acid molecules are available the nucleic acids are amplified (e.g., by whole genome amplification) prior to practicing the method of the present invention. For example, prior amplification may be necessary for performing embodiments of the present invention for forensic purposes (e.g., in forensic medicine, etc.).

It is contemplated that in preferred embodiments, the population of nucleic acid molecules is a population of genomic DNA molecules. The hybridization probes and subsequent amplicons may comprise one or more sequences that target a plurality of exons, introns or regulatory sequences from a plurality of genetic loci, the complete sequence of at least one single genetic locus, said locus having a size of at least 100 kb, preferably at least 1 Mb, or at least one of the sizes as specified above, sites known to contain SNPs, or sequences that define an array, in particular a tiling array, designed to capture the complete sequence of at least one complete chromosome.

It is contemplated that target nucleic acid sequences are enriched from one or more samples that include nucleic acids from any source, in purified or unpurified form. The source need not contain a complete complement of genomic nucleic acid molecules from an organism. The sample, preferably from a biological source, includes, but is not limited to, pooled isolates from individual patients, tissue samples, or cell culture. The target region can be one or more continuous blocks of several megabases, or several smaller contiguous or discontiguous regions, such as all of the exons from one or more chromosomes, or sites known to contain SNPs. For example, the hybridization probes and subsequent probe derived amplicons can support a tiling array designed to capture one or more complete chromosomes, parts of one or more chromosomes, all exons, all exons from one or more chromosomes, selected exons, introns and exons for one or more genes, gene regulatory regions, and so on.

Alternatively, to increase the likelihood that desired non-unique or difficult-to-capture targets are enriched, the probes can be directed to sequences associated with (e.g., on the same fragment as, but separate from) the actual target sequence, in which case genomic fragments containing both the desired target and associated sequences will be captured and enriched. The associated sequences can be adjacent or spaced apart from the target sequences, but a skilled person will appreciate that the closer the two portions are to one another, the more likely it will be that genomic fragments will contain both portions. To reduce the limited impact of cross-hybridization by off-target molecules, thereby enhancing the integrity of the enrichment, sequential rounds of capture using distinct but related capture probe sets, and thus probe derived amplicons, directed to the target region is performed. Related probes are probes corresponding to regions in close proximity to one another in the genome that hybridize to the same genomic DNA fragment.

In some embodiments of the present invention, the methods comprise the step of ligating adaptor or linker molecules to one or both ends of the nucleic acid molecules prior to denaturation and hybridization to the probe amplicons in solution.

In some embodiments of the present invention the methods further comprise amplifying said adaptor modified nucleic acid molecules with at least one primer, said primer comprising a sequence which specifically hybridizes to the sequence of said adaptor molecule (s).

In some embodiments of the present invention, double-stranded linkers are provided at one or both ends of the fragmented nucleic acid molecules before sample denaturation and hybridization to the probe derived amplicons in solution. In such embodiments, target nucleic acid molecules are amplified after elution to produce a pool of amplified products having further reduced complexity relative to the original sample. The target nucleic acid molecules can be amplified using, for example, non-specific Ligation Mediated-PCR (LM-PCR) through multiple rounds of amplification and the products can be further enriched, if required, by one or more rounds of selection against the amplicon derived probes. The linkers or adaptors are provided, for example, in an arbitrary size and with an arbitrary nucleic acid sequence according to what is desired for downstream analytical applications subsequent to the complexity reduction step. The linkers can range between about 12 and about 100 base pairs, including a range between about 18 and 100 base pairs, and preferably between about 20 and 24 base pairs. Adaptor molecules in the context of the present invention are preferably defined as blunt-ended double-stranded oligonucleotides.

In order to ligate adaptor molecules onto a double stranded target molecule, it is preferred that this target molecule itself is blunt ended. In order to achieve this, the double stranded target molecules are subjected to, for example, a fill-in reaction with a DNA Polymerase such as T4 DNA polymerase or Klenow polymerase in the presence of dNTPs, which results in blunt ended target molecules. In addition, ends of the fragments are phosphorylated using T4 Polynucleotide kinase and methods known to skilled artisans (for example, see Molecular Cloning: A Laboratory Manual, Eds. Sambrook et al., Cold Spring Harbour Press; incorporated herein by reference in its entirety) to add phosphate groups to the 5' termini of the fragments prior to the ligation of the adaptors. Subsequent ligation of the adaptors (e.g., short double stranded blunt end DNA oligo-nucleotides with about 3-20 base pairs) onto the polished, phosphorylated target DNA may be performed according to any method which is known in the art, for example by T4 DNA ligase reaction.

The ligation of the adaptors to the fragmented target nucleic acid molecules may be performed prior to, or after, exposing a sample that comprises fragmented, denatured genomic nucleic acid molecules to multiple oligonucleotide probes amplicons in solution under hybridizing conditions to capture target nucleic acid molecules. When ligation is performed after hybridization, the enriched nucleic acids which are released from the amplicons in single stranded form are initially re-annealed followed by a primer extension reaction and a fill-in reaction according to standard methods known in the art.

Ligation of adaptor molecules allows for a step of subsequent amplification of the captured molecules. Independent from whether ligation takes place prior to or after the capturing step, there exist several alternative embodiments. In one embodiment, one type of adaptor molecule (e.g., adaptor molecule A) is ligated that results in a population of fragments with identical terminal sequences at both ends of the fragment. As a consequence, it is sufficient to use only one primer in a potential subsequent amplification step. In an alternative embodiment, two types of adaptor molecules A and B are used. This results in a population of enriched molecules composed of three different types: (i) fragments having one adaptor (A) at one end and another adaptor (B) at the other end, (ii) fragments having adaptors A at both ends, and (iii) fragments having adaptors B at both ends. The generation of enriched molecules with adaptors is of outstanding advantage, if amplification and sequencing is to be performed, for example using the 454 Life Sciences Corporation GS20 and GSFLX instrument (e.g., see GS20 Library Prep Manual, December 2006, WO 2004/070007; incorporated herein by reference in their entireties).

The present invention is directed to a method for detecting coding region variation(s) of a test genome sample relative to a reference genome sample, in particular relative to a reference genome that comprises fragmented, denatured genomic nucleic acid molecules, the method comprising the steps as previously described on both a test and reference genome, further comparing the sequences to a sequence in a database, in particular to a sequence in a database of polymorphisms in a reference genome sample to identify variants from a test genome sample. The invention is, therefore, useful in searching for genetic variants and mutations, such as single nucleotide polymorphisms (SNP), or set of SNPs, genomic insertions and/or deletions, translocations, etc. that may underlie human diseases. It is contemplated that capture and enrichment using solution based hybridization technology as described herein is more flexible than other methods currently available in the field of genomic enrichment.

In some embodiments of the present invention, the eluted target nucleic acid sequences may be sequenced, hybridized to a resequencing or SNP-calling array and the sequence or genotypes may be further analyzed. Solution based enrichment as provided by embodiments of the present invention enables targeted array-based-, shotgun-, capillary-, or other sequencing methods known in the art. In general, strategies for shotgun sequencing of randomly generated fragments are cost-effective and readily integrated into a pipeline. The present invention enhances the efficiency of the shotgun approach by presenting only fragments from one or more genomic regions of interest for sequencing. The invention provides an ability to focus the sequencing strategies on specific genomic regions, such as individual chromosomes or exons for medical sequencing purposes. As such, a more focused approach to disease discovery is realized.

In embodiments of the present invention, the eluted target nucleic acid sequences resulting from solution based enrichment methods as described herein, are subsequently sequenced. Sequencing can be performed by a number of different methods, such as by employing sequencing by synthesis technology. Sequencing by synthesis according to the prior art is defined as any sequencing method which monitors the generation of side products upon incorporation of a specific deoxynucleoside-triphosphate during the sequencing reaction (Hyman, 1988, Anal. Biochem. 174: 423-436; Rhonaghi et al., 1998, Science 281:363-365). One prominent embodiment of the sequencing by synthesis reaction is the pyrophosphate sequencing method. In this case, generation of pyrophosphate during nucleotide incorporation is monitored by an enzymatic cascade which results in the generation of a chemo-luminescent signal. The 454 Genome Sequencer System (Roche Applied Science cat. No. 04 760 085 001), an example of sequence by synthesis, is based on the pyrophosphate sequencing technology. For sequencing on a 454 GS20 or 454 FLX instrument, the average genomic DNA fragment size is in the range of 200 or 600 bp, respectively, as described in the product literature.

A sequencing by synthesis reaction can alternatively be based on a terminator dye type of sequencing reaction. In this case, the incorporated dye deoxynucleotriphosphates (ddNTPs) building blocks comprise a detectable label, which is preferably a fluorescent label that prevents further extension of the nascent DNA strand. The label is then removed and detected upon incorporation of the ddNTP building block into the template/primer extension hybrid for example by using a DNA polymerase comprising a 3'-5' exonuclease or proofreading activity.

In case of the Genome Sequencer workflow (Roche Applied Science Catalog No. 04 896 548 001), in a first step, (clonal) amplification is performed by emulsion PCR. Thus, it is also within the scope of the present invention, that the step of amplification is performed by emulsion PCR methods. The beads carrying the clonally amplified target nucleic acids may then become arbitrarily transferred into a picotiter plate according to the manufacturer's protocol and subjected to a pyrophosphate sequencing reaction for sequence determination.

In some embodiments, the present invention comprises a kit comprising reagents and materials for performing methods according to the present invention. Such a kit may include one or more of a microarray substrate upon which is immobilized a plurality of hybridization probes specific to one or more target nucleic acid sequences from one or more target genetic loci (e.g., specific to exons, introns, SNP sequences, etc.), a plurality of probes that define a tiling array designed to capture the complete sequence of at least one complete chromosome, amplification primers, reagents for performing polymerase chain reaction methods (e.g., salt solutions, polymerases, dNTPs, amplification buffers, etc.), reagents for performing ligation reactions (e.g., ligation adaptors, T4 polynucleotide kinase, ligase, buffers, etc.), substrates comprising a binding partner moiety, tubes, hybridization solutions, wash solutions, elution solutions, magnet(s), and tube holders.

In some embodiments, the present invention provides a system (e.g., kit) for performing a method or part of a method according to the present invention as disclosed herein. Thus, the present invention is a kit comprising a (first) double stranded adaptor molecule and multiple probe derived amplicons in solution, wherein the probe derived amplicons are amplified from a plurality of probes that defines a plurality of exons, introns and/or regulatory sequences from a plurality of genetic loci, and/or a plurality of probe derived amplicons in solution that defines the complete sequence of at least one single genetic locus, said locus having a size of at least 100 kb, preferably at least 1 Mb or a size as specified herein, and/or a plurality of probe derived amplicons that defines sites known to contain SNPs, and/or a plurality of probe derived amplicons that defines an array, in particular a tiling array especially designed to capture the complete sequence of at least one complete chromosome. In some embodiments, a kit further comprises two different double stranded adaptor molecules.

In some embodiments, a kit comprises one or more capture molecules or compounds. For example, at least one oligonucleotide probe comprises a modification which allows for immobilization onto a solid support. For example, a probe comprises a biotin moiety for immobilization onto a streptavidin coated paramagnetic particle. Another example is a hapten, such as digoxigenin, that is associated with a probe for immobilization on a solid support using a hapten recognizing antibody (e.g., anti-digoxigenin).

In some embodiments, a kit further comprises at least one or more compounds from a group consisting of DNA polymerase, T4 polynucleotide kinase, T4 DNA ligase, one or more array hybridization solutions, and/or one or more array wash solutions. In preferred embodiments, three wash solutions are included in a kit of the present invention, the wash solutions comprising SSC, DTT and optionally SDS. For example, kits of the present invention comprise Wash Buffer I (0.2% SSC, 0.2% (v/v) SDS, 0.1 mM DTT), Wash Buffer II (0.2% SSC, 0.1 mM, DTT) and/or Wash Buffer III (0.05% SSC, 0.1 mM DTT). In some embodiments, systems of the present invention further comprise an elution solution, for example water or a solution containing TRIS buffer and/or EDTA.

EXPERIMENTATION

The following examples are provided in order to demonstrate and further illustrate certain preferred embodiments and aspects of the present invention and are not to be construed as limiting the scope thereof.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Example 1

Discovery of New Polymorphisms and Mutations in Large Genomic Regions

This generic example describes how to perform selection that allows for rapid and efficient discovery of new polymorphisms and mutations in large genomic regions.

Microarrays having immobilized probes are used in one- or multiple rounds of hybridization selection with a target of total genomic DNA, and the selected sequences are amplified by LM-PCR a) Preparation of the Genomic DNA and Double-Stranded Linkers DNA is fragmented using sonication to an average size of 500 base pairs. A reaction to polish the ends of the sonicated DNA fragments is setup:

| | |
|---|---|
| DNA fragments | 41 µl |
| T4 DNA Polymerase | 20 µl |
| T4 DNA polymerase reaction mix | 20 µl |
| Water | 10 µl |

The reaction is incubated at 11° C. for 30 min. The reaction is then subjected to phenol/chloroform extraction procedures and the DNA is recovered by ethanol precipitation. The precipitated pellet is dissolved in 10 µl water (to give a final concentration of 2 µg/µl).

Two complementary oligonucleotides are annealed to create a double-stranded linker, by mixing the following:

| | |
|---|---|
| Oligonucleotide 1 (1 µg/µl)<br>(5'-CTCGAGAATTCTGGATCCTC-3')<br>(SEQ ID NO: 1) | 22.5 µl |
| Oligonucleotide 2 (1 µg/ul)<br>(5'-GAGGATCCAGAATTCTCGAGTT-3')<br>(SEQ ID NO: 2) | 22.5 µl |
| 10x annealing buffer | 5 µl |
| Water | to 50 µl |

The reaction is heated at 65° C. for 10 min; then allowed to cool at 15-25° C. for 2 hours. The length of the 2 complementary oligonucleotides 1 and 2 is between 12 and 24 nucleotides, and the sequence is selected depending upon the functionality desired by the user. The double-stranded linker is then purified by column chromatography through a Sephadex G-50 spin column. The purified linker solution is then concentrated by lyophilization to a concentration of 2 µg/µl.

b) Ligation of Linkers to Genomic DNA Fragments

The following reaction to ligate the linkers to genomic DNA fragments is set up. The reaction is incubated at 14° C. overnight.

| | |
|---|---|
| Annealed linkers from Step a) (20 µg) | 10 µl |
| Genomic DNA from Step a) (10 µl) | 5 µl |
| T4 DNA ligase | 10 U |
| 10x ligation buffer | 2 µl |
| Water | to 20 µl |

The reaction volume is adjusted to 500 µl with water and the ligated genomic DNA is purified using a QIAquick PCR purification kit. The purified DNA is stored at a concentration of 1 µg/µl.

c) Primary Selection and Capture of Hybrid

To prepare the genomic DNA sample for hybridization to the microarray, linker modified genomic DNA (10 µg) is resuspended in 3.5 µl of nuclease-free water and combined with 31.5 µl NimbleGen Hybridization Buffer (Roche NimbleGen, Inc., Madison, Wis.), 9 µl Hybridization Additive (Roche NimbleGen, Inc), in a final volume of 45 µl. The samples are heat-denatured at 95° C. for 5 minutes and transferred to a 42° Cheat block.

To capture the target genomic DNA on the microarray, samples are hybridized to NimbleGen CGH arrays, manufactured as described in U.S. Pat. No. 6,375,903 (Roche NimbleGen, Inc.). Maskless fabrication of capture oligonucleotides on the microarrays is performed by light-directed oligonucleotide synthesis using a digital micromirror as described in Singh-Gasson et al. (1999, Nat. Biotech. 17:974-978, incorporated herein by reference in its entirety) as performed by a maskless array synthesizer. Gene expression analysis using oligonucleotide arrays produced by maskless photolithography is described in Nuwaysir et al. (2002, Genome Res. 12:1749-1755, incorporated herein by reference in its entirety). Hybridization is performed in a MAUI Hybridization System (BioMicro Systems, Inc., Salt Lake City, Utah) according to manufacturer instructions for 16 hours at 42° C. using mix mode B. Following hybridization, arrays are washed twice with Wash Buffer I (0.2× SSC, 0.2% (v/v) SDS, 0.1 mM DTT, NimbleGen Systems) for a total of 2.5 minutes. Arrays are then washed for 1 minute in Wash Buffer II (0.2×SSC, 0.1 mM DTT, NimbleGen Systems) followed by a 15 second wash in Wash Buffer III (0.05×SSC, 0.1 mM DTT, Roche NimbleGen, Inc.).

To elute the genomic DNA hybridized to the microarray, the arrays are incubated twice for 5 minutes in 95° C. water. The eluted DNA is dried down using vacuum centrifugation.

d) Amplification of the Primary Selected DNA

The primary selected genomic DNA is amplified as described below. Ten separate replicate amplification reactions are set up in 200 µl PCR tubes. Only one oligonucleotide primer is required because each fragment has the same linker ligated to each end:

Reaction Reagents:

| | |
|---|---|
| Template: primary selection material | 5 µl |
| Oligonucleotide 1 (200 ng/µl)<br>(5'-CTCGAGAATTCTGGATCCTC-3')<br>(SEQ ID NO: 1) | 1 µl |
| dNTPs (25 mM each) | 0.4 µl |
| 10x PfuUltra HF DNA polymerase Reaction buffer | 5 µl |
| PfuUltra HF DNA polymerase | 2.5 U |
| Water | to 50 µl |

The reactions are amplified according to the following program:

| Cycle number | Denaturation | Annealing | Polymerization |
|---|---|---|---|
| 1 | 2 min at 95° C. | | |
| 2-31 | 30 sat 95° C. | 30 sat 55° C. | 1 min at 72° C. |

The reaction products are analyzed by agarose gel electrophoresis. The amplification products are purified using a QIAquick PCR purification kit. The eluted samples are pooled and the concentration of amplified primary selected DNA is determined by spectrophotometry. A volume of DNA in the pool equivalent to 1 µg is reduced to 5 µl in a speed vacuum concentrator. One µl (at least 200 ng) of the primary selected material is set aside for comparison with the secondary selection products. As necessary, subsequent rounds of enrichment are performed by further rounds of array hybridization and amplification of the eluted sample.

e) Preparation of Target Oligonucleotide Probes for Release from Micro array and Immobilization on Support Probes are synthesized on a microarray, then are released using a base-labile Fmoc (9-fluorenylmethyloxycarbonyl) group. The probes are labelled with biotin and are then immobilized onto the surface of a streptavidin solid support using known methods for covalent or non-covalent attachment.

Optionally, prior to immobilization onto the solid support, the synthesized probes are amplified using LM-PCR, Phi29 or other amplification strategy to increase the amount of the synthesized probes by virtue of inserting sequences upon them that facilitate their amplification. This material can now be used for direct sequencing, array based resequencing, genotyping, or any other genetic analysis targeting the enriched region of the genome by employing solution phase hybridization and SA mediated capture of the hybridization products.

Example 2

Array-Targeted Resequencing

A series of high-density oligonucleotide microarrays that capture short segments that correspond to 6,726 individual gene exon regions of at least 500 base pairs were chosen from 660 genes distributed about the human genome (sequence build HG 17) (approximately 5 Mb of total sequence) were synthesized according to standard Roche NimbleGen, Inc. microarray manufacturing protocols. Overlapping microarray probes of more than 60 bases each on the array spanned each target genome region, with a probe positioned each 10 bases for the forward strand of the genome.

Highly-repetitive genomic regions were excluded by design from the capture microarrays, to reduce the likelihood of non-specific binding between the microarrays and genomic nucleic acid molecules. The strategy for identifying and excluding highly-repetitive genomic regions was similar to that of the WindowMasker program (Morgulis et al.). The average 15-mer frequency of each probe was calculated by comparing the frequencies of all 15-mers present in the probe against a pre-computed frequency histogram of all possible 15-mer probes in the human genome. The likelihood that the probe represents a repetitive region of the genome increases as the average 15-mer frequency increases. Only probes having an average 15-mer frequency below 100 were included on the capture microarrays.

To test the reproducibility of the capture system, the exonic design was first used to capture fragmented genomic DNA from a human cell line (Burkitt's Lymphoma, NA04671 (Coriell)). Briefly, genomic DNA (20 µg) was subjected to whole genome amplification (WGA; using Qiagen service (Hilden, Germany)). Twenty µg of the WGA product was treated with Klenow fragment of DNA polymerase I (NEB, Beverly Mass.) to generate blunt-ends. The blunt-ended fragments were sonicated to generate fragments of about 500 base pairs and then 5' phosphorylated with polynucleotide kinase (NEB). Oligonucleotide linkers 5'-PiGAGGATCCAGAATTCTCGAGTT-3' (SEQ ID NO:2) and 5'-CTCGAGAATTCTGGATCCTC-3' (SEQ ID NO: 1) were annealed and ligated to the ends of the 5' phosphorylated fragments:

The linker-terminated fragments were denatured to produce single stranded products that were exposed to the capture microarrays under hybridization conditions in the presence of 1× hybridization buffer (Roche NimbleGen, Inc.) for approximately 65 hours at 42° C. with active mixing using a MAUI hybridization station (Roche NimbleGen, Inc.). Single-stranded molecules that did not hybridize were washed from the microarrays under stringent washing conditions, 3×5 minutes with Stringent Wash Buffer (Roche NimbleGen, Inc.) and rinsed with Wash Buffers I, II, and III (Roche NimbleGen, Inc.). Fragments captured on the microarrays were immediately eluted with 2×250 µl of water at 95° C., dried and resuspended for amplification by LM-PCR using a primer complementary to the previously ligated linkers oligonucleotides.

To quantify enrichment of the exonic regions, eight random regions were selected for quantitative PCR (qPCR). These regions were amplified using the following primers:

```
Region 1
                                        (SEQ ID NO: 3)
    F: 5'-CTACCACGGCCCTTTCATAAAG-3'

(SEQ ID NO: 4)
    R: 5'-AGGGAGCATTCCAGGAGAGAA-3'

Region 2
                                        (SEQ ID NO: 5)
    F: 5'-GGCCAGGGCTGTGTACAGTT-3'

(SEQ ID NO: 6)
    R: 5'-CCGTATAGAAGAGAAGACTCAATGGA-3'

Region 3
                                        (SEQ ID NO: 7)
    F: 5'-TGCCCCACGGTAACAGATG-3'

(SEQ ID NO: 8)
    R: 5'-CCACGCTGGTGATGAAGATG-3'

Region 4
                                        (SEQ ID NO: 9)
    F: 5'-TGCAGGGCCTGGGTTCT-3'

(SEQ ID NO: 10)
    R: 5'-GCGGAGGGAGAGCTCCTT-3'

Region 5
                                       (SEQ ID NO: 11)
    F: 5'-GTCTCTTTCTCTCTCTTGTCCAGTTTT-3'

(SEQ ID NO: 12)
    R: 5'-CACTGTCTTCTCCCGGACATG-3'

Region 6
                                       (SEQ ID NO: 13)
    F: 5'-AGCCAGAAGATGGAGGAAGCT-3'

(SEQ ID NO: 14)
    R: 5'-TTAAAGCGCTTGGCTTGGA-3'

Region 7
                                       (SEQ ID NO: 15)
    F: 5'-TCTTTTGAGAAGGTATAGGTGTGGAA-3'

(SEQ ID NO: 16)
    R: 5'-CAGGCCCAGGCCACACT-3'

Region 8
                                       (SEQ ID NO: 17)
    F: 5'-CGAGGCCTGCACAGTATGC-3'

(SEQ ID NO: 18)
    R: 5'-GCGGGCTCAGCTTCTTAGTG-3'
```

After a single round of microarray capture, the enriched, amplified samples and control genomic DNA, that was fragmented, linker-ligated and LM-PCR amplified, but not hybridized to a capture array, were compared using an ABI 7300 real time PCR system (Applied Biosystems, Foster City, Calif.) measuring SYBR green fluorescence according to manufacturer's protocols. An average of 378-fold enrichment was achieved for three replicate exonic capture products. The theoretical maximum enrichment level was 600 fold (3,000 Mb in the genome and 5 Mb of total sequence).

Samples eluted from the capture microarrays were ligated to 454-sequencing-compatible linkers, amplified using emulsion PCR on beads and sequenced using the 454 FLX sequencing instrument (454, Branford Conn.). Because each sequenced fragment also contained the 20 bp LM-PCR linker used immediately after microarray elution, the majority of 454 sequencing reads contained that linker sequence. DNA sequencing of the three replicates on the 454 FLX instrument generated 63 Mb, 115 Mb, and 93 Mb of total sequence. Following in silico removal of the linker sequence, each sequencing read was compared to the entire appropriate version of the Human Genome using BLAST analysis (Altschul, et al., 1990, J. Mol. Biol. 215:403-410; incorporated herein by reference in its entirety) using a cutoff score of e=10-48, tuned to maximize the number of unique hits. Reads that did not uniquely map back to the genome (between 10 and 20%) were discarded. The rest were considered captured sequences. Captured sequences that, according to the original BLAST comparison, map uniquely back to regions within the target regions were considered sequencing hits. These were then used to calculate the % of reads that hit target regions, and the fold sequencing coverage for the entire target region. Data was visualized using SignalMap software (Roche NimbleGen, Inc.).

BLAST analysis showed that 91%, 89%, and 91% of reads, respectively, mapped back uniquely to the genome; 75%, 65%, and 77% were from targeted regions and 96%, 93%, and 95% of target sequences contained at least one sequence read (Table 1, upper three rows) representing an average enrichment of about 400 fold. The median per-base coverage for each sample was 5-, 7- and 7-fold coverage respectively.

TABLE 1

| DNA Sample | qPCR Fold Enrichment | FLX - Yield (Mb) | Percentage of Reads Mapped Uniquely to the Genome | Percentage of Total Reads That Mapped to Selection Targets | Median Fold Coverage for Target Regions |
|---|---|---|---|---|---|
| NA04671 | 318 | 63.1 | 91% | 75% | 5 |
| NA04671 | 399 | 115 | 89% | 65% | 7 |

TABLE 1-continued

| DNA Sample | qPCR Fold Enrichment | FLX - Yield (Mb) | Percentage of Reads Mapped Uniquely to the Genome | Percentage of Total Reads That Mapped to Selection Targets | Median Fold Coverage for Target Regions |
|---|---|---|---|---|---|
| NA04671 | 418 | 93.0 | 91% | 76% | 7 |
| HapMap EPH | 217 | 77.6 | 88% | 74% | 7 |
| HapMap JPT | 153 | 96.7 | 84% | 66% | 8 |
| HapMap HB | 240 | 52.8 | 83% | 59% | 4 |
| HapMap YRI | 363 | 81.3 | 53% | 58% | 4 |

Example 3

Sequence Variation Captured by Genomic Enrichment and Resequencing

To ascertain the ability to discern variation in the human genome, genomic DNA samples from four cell types in the human HapMap collection (CEPH/NA11839, CHB/NA18573, JPT/NA18942, YR1/NA18861, Coriell) were captured on the exon arrays of the prior examples, eluted and sequenced, as disclosed herein, except that the genomic DNAs were not whole genome amplified before capture. The capture results (shown in Table 1, rows 4-7) were similar to those above, except that sequence coverage was consistently more uniform than before, suggesting a bias introduced during WGA.

The sequence from the four HapMap samples was assembled and mutations were identified and compared to the HapMap SNP data for each sample (Tables 1 and 2). The total number of positions in the target regions that were genotyped in the HapMap project was 8103 (CEU), 8134 (CHB), 8134 (JPT), 8071 (YR1) for each of the four genomes. Of these, most (~6000) sites were homozygous for the reference genome allele. The number of known variant alleles (homozygous or heterozygous) is listed in the second row of Table 2. These positions were analyzed for coverage and to determine whether the allele(s) were found in the captured DNA.

TABLE 2

| Pop/Indiv | CEPH/NA11839 | CHB/NA18573 | JPT/NA18942 | CEPH/NA11839 |
|---|---|---|---|---|
| # Known variant alleles | 2235 | 2257 | 2206 | 2334 |
| Stringency of at least one read per known variant Hap Map allele | | | | |
| Positions with ≥1 read | 2176 (97.3%) | 2104 (93.2%) | 2168 (98.2%) | 2133 (91.3%) |
| Variant alleles found in ≥1 read | 2071 (92.6%) | 1922 (85.1%) | 2080 (94.2%) | 1848 (79.1%) |
| False negative rate | 7.4% | 14.9% | 5.8% | 20.9% |
| Stringency of at least two reads per known variant HapMap allele | | | | |
| Positions with ≥1 read | 2176 (97.3%) | 2104 (93.2%) | 2168 (98.2%) | 2133 (91.3%) |
| Variant alleles found in ≥2 reads | 1907 (85.3%) | 1569 (69.5%) | 1939 (87.8%) | 1469 (62.9%) |
| False negative rate | 14.7% | 30.5% | 12.2% | 37.1% |

Between 94% and 79% of known variant positions among the HapMap samples were identified with at least one sequence read, which was expected, based upon the overall sequence coverage. There was no apparent biasing against alleles not present on the capture array when coverage of targets that contained 0, 1 or >1 known variants, (7.95, 8.48, and 8.82 fold coverage respectively) were compared.

There is considerable interest in the analysis of large contiguous genomic regions. Capture microarray series that target single long segments from 200 kb-5 Mb surrounding the human BRCA1 gene were tested with the NA04671 DNA. For array series used to capture the BRCA1 gene locus, five genomic regions of increasing size (200 kb, 500 kb, 1 Mb, 2 Mb, and 5 Mb) surrounding the BRCA1 gene locus were chosen from the human genome sequence (build HG 18). Attributes of the locus-capture arrays are shown in Table 3. The average probe tiling density is the average distance between the start of one probe and the start of the next probe.

TABLE 3

| BRCA1 Region Size | Average Selection Probe Tiling Density (base pairs) | Chromosome 17 coordinates (HG18) |
|---|---|---|
| 200 kb | 1 bp | 38,390,417-38,590,417 |
| 500 kb | 1 bp | 38,240,417-38,740,417 |
| 1 Mb | 2 bp | 37,990,417-38,990,417 |
| 2 Mb | 3 bp | 37,490,417-39,490,417 |
| 5 Mb | 7 bp | 35,990,417-40,990,417 |

Table 4 shows that all capture targets performed well, with up to 140 Mb of raw sequence generated in a single sequencing machine run, generating 18 fold coverage, from a 5 Mb capture region. It was demonstrated that the percentage of reads that map to the target sequence increased with the size of the target region.

TABLE 4

| Tiling Size (kb) | Average Selection Probe Tiling Density | FLX-Yield (Mb) | Percentage of Reads Mapped Uniquely to the Genome | Percentage of Total Reads That Mapped to Selection Targets | Median fold coverage of Unique Portion of Region |
|---|---|---|---|---|---|
| 200 | 1 bp | 102 | 55% | 14% | 79 |
| 500 | 1 bp | 85.0 | 61% | 36% | 93 |
| 1,000 | 2 bp | 96.7 | 56% | 35% | 38 |
| 2,000 | 3 bp | 112.6 | 81% | 60% | 37 |
| 5,000 | 7 bp | 140 | 81% | 64% | 18 |

These data illustrate the power of microarray-based direct selection methods for enriching targeted sequences. The inventor used a programmable high-density array platform with 385,000 probes that were readily able to capture at least 5 Mb of total sequence. In addition to the specificity of the assay, the high yields of the downstream DNA sequencing steps are consistently superior to the routine average performance using non-captured DNA sources. This is attributed to the capture-enrichment process providing a useful purification of unique sequences away from repeats and other impurities that can confound, for example, the first emulsion PCR step of the 454 sequencing process.

Example 4

Solution Phase Capture and Resequencing

The sample of Examples 2 and 3 was tested using capture probes synthesized upon, then liberated from, a solid support such that the enrichment was advantageously executed in solution phase. Standard micro array designs (e.g. the BRCAI 200K Tiling array and human exon capture arrays of the prior examples) were modified by adding terminal 15 mer primer sequences containing an MlyI recognition site, which facilitates enzymatic primer removal while leaving the capture oligonucleotide sequence intact.

Arrays were synthesized by adding chemical phosphorylating reagent (Glen Research) after the initial T5 linker and before the 3' primer sequence. Three individual couplings were performed to maximize subsequent cleavage of capture probes from the arrays.

The array-immobilized capture probes were treated with 30% ammonium hydroxide ($NH_4OH$, Aldrich). After synthesis, arrays were placed in a humid chamber and approximately 700 µl of $NH_4OH$ was applied to the synthesis area at ambient room temperature for 20 minutes to cleave the probes from the array. The $NH_4OH$ remained largely within the confines of the synthesis area because of hydrophobicity differences between the reaction area and the surrounding glass. The solution was removed using a pipette and was retained. An additional 700 µl of fresh $NH_4OH$ was applied to the surface. The process was repeated for a total of 3× (60 min and 2.1 ml total). Cleaved oligonucleotide capture probes were then dried by centrifugation under vacuum under standard conditions known in the art The cleaved capture probes were amplified under standard conditions. Dried probes were resuspended in 30 µl deionized water ($diH_2O$) and aliquoted into 30 individual PCR runs as follows:

Reaction Reagents:

| | |
|---|---|
| 10x buffer | 2.5 µl |
| 25 mM dNTPs | 0.125 µl |
| 20 µM Primer 1a | 1.25 µl |
| 20 µM Primer 1b (biotinylated) | 1.25 µl |
| HotStart Taq | 0.25 µl |
| $MgCl_2$ | 1 µl |
| Sample | 1 µl |
| $H_2O$ | 17.625 µl |
| Total volume | 25 µL |

Primer 1a:
5'-TGCCGGAGTCAGCGT-3' (SEQ ID NO: 19)

Primer 1b:
5'-Biotin-AGTCAGAGTCGCCAC-3' (SEQ ID NO: 20)

The reactions are amplified according to the following program:

| Cycle number | Denaturation | Annealing | Polymerization |
|---|---|---|---|
| 1 | 15 min at 95° C. | | |
| 2-31 | 20 s at 95° C. | 45 s at 48° C. | 20 s at 72° C. |

PCR products were purified away from reaction components using the QiaQuick Nucleotide Removal Kit (Qiagen), dried and resuspended in 20 µl $diH_2O$. Typical yield after purification was approximately 400-700 ng/rxn by Nanodrop. Amplicons may be checked on a 3% agarose gel. Depending on quantity requirements of capture probes, additional PCR rounds were performed as above yielding approximately 200 ng of sample per reaction. Amplicons were purified and characterized as above.

The final round of amplification of the capture probes was performed using asymmetric PCR. The protocol was as above, except that while the biotinylated primer concentration remained the same, the non-biotinylated primer concentration was reduced to 0.001× of the original concentration. The protocol was extended to 35 cycles to allow for non-exponential amplification. Amplicons were dried, resuspended in 20 µl diH$_2$O, and characterized.

The genomic DNA sample was prepared per standard protocol; 20 µg of WGA Tinkered sample was dried with 100 µg Cot-1 DNA and resuspended in 7.5 µl hybridization buffer and 3 µl formamide. A 2 µg aliquot of capture probes was dried and resuspended in 4.5 µl diH$_2$O. The sample solution was mixed with the capture probe solution and incubated at 95° C. for 10 minutes. The mixture was then transferred to a PCR tube and placed in a thermal cycler for 3 days at 42° C. for hybridization to form duplexes.

After hybridization, the duplexes were bound to paramagnetic beads (Dynal). 25 µl of beads were washed three times in 2× BW buffer (10 mM Tris HCl, 1 mM EDTA, 2M NaCl), and the beads were resuspended in the hybridization mixture. Binding occurred over 45 minutes at 42° C. with occasional gentle mixing.

Bound beads were isolated using a magnet and washed briefly with 40 µl Wash Buffer I, incubated for 2×5 minutes in 47° C. stringent wash buffer, washed with Wash Buffer I for approximately 2 minutes at ambient room temperature, with Wash Buffer II for approximately 1 minute, and with Wash Buffer III for approximately 30 seconds.

To elute the captured fragments, the solution containing beads in Wash Buffer III was transferred to a 1.5 ml Eppendorf tube. The beads were isolated with a magnet. The wash buffer was removed and ~100 µl of 95° C. diH$_2$O is added. The solution was incubated at 95° C. for 5 minutes, after which the beads were bound with a magnet and gently washed with 95° C. diH$_2$O. The wash liquid was then removed and retained, and replaced with fresh 95° C. diH$_2$O. Incubation and washing was repeated for a total of 3 times (15 minutes, approximately 300 µl eluate). After the final wash, the Eppendorf tube containing eluate is placed on a magnetic stand for approximately 5 minutes to isolate any beads aspirated during elution. The solution was dried at high heat in a fresh Eppendorf tube. The eluted captured fragments were resuspended in 263 µl diH$_2$O prior to standard LM-PCR.

Following LM-PCR, the captured fragments were subjected to standard ultra-deep sequencing using the 454 FLX platform, as above. Alternatively, LM-PCR can be avoided by ligating 454 sequencing adapter sequences to the pre-enrichment sample. In that case, the eluted enriched sequences can be piped directly into the emulsion PCR for ultra-deep sequencing.

Data indicated that 83.8% of the reads map back to target regions, which is comparable and indistinguishable from results obtained using array-based capture protocols.

Example 5

Solution Phase Capture Using In Situ Amplification of Capture Probes

A standard microarray design was modified by addition of a terminal 15 mer primer sequence containing a MlyI (GAGTC(5/5)) recognition site. Incorporation of a MlyI site into the primer sequence facilitates enzymatic primer removal while leaving the capture oligonucleotide sequences intact. Arrays were synthesized via standard maskless array synthesis methods known to those skilled in the art.

Capture probes were amplified using in situ polymerase chain reaction (PCR) on an array in a thermal cycler using a sealing hybridization chamber (Grace Bio-Labs, Inc., Bend, Oreg.) and Slide Griddle Adaptor (Bio-Rad Laboratories, Hercules, Calif.). PCR reaction constituents (25 µl of 10× polymerase buffer, 1.25 µl of 25 mM dNTPs, 12.5 µl each of 20 µM primer 1a and 1b, 2.5 µl of Hotstart Taq polymerase, 10 µl 25 mM MgCl$_2$ and 176.5 µl diH$_2$O, total reaction volume of 250 µl) were added to the microarray hybridization chambers and PCR was performed using the conditions; 100° C. for 30 s, 97° C. for 15 min., 30 cycles of 100° C. for 30 s, 47.5° C. for 45 s, 78° C. for 30 s followed by cooling the reactions down to 1° C. for 30 s and 3.5° C. to hold. Primer sequences were primer 1a 5'-TGCCG-GAGTCAGCGT-3' (SEQ ID NO: 19) and primer 1b 5'-Biotin-AGTCAGAGTCGCCAC-3' (SEQ ID NO: 20), reflecting primer binding sites that were incorporated into the probe sequences.

Polymerase chain reaction capture probe amplicons were purified from the reaction components using the QIAquick® Nucleotide Removal Kit (Qiagen, Inc., Valencia, Calif.), dried down and resuspended in 20 µl diH$_2$O. Amplification yield was roughly 5 µg total as measured by NanoDrop® spectrophotometry (Thermo Fisher Scientific). Additional amplification rounds, following the protocol above, can be performed if additional amplicon quantity is needed (e.g., using the above protocol and 100 ng sample per reaction).

The final round of amplification of the capture probes was performed using asymmetric PCR; 2.5 µl 10× polymerase buffer, 0.125 µl 25 mM dNTPs, 0.0125 µl of 20 µM primer 1a, 1.25 µl of 20 µM primer 1b, 0.25 µl Hotstart Taq, 1 µl 25 mM MgCl$_2$ and 18.86 µl diH$_2$O (total reaction volume of 25 µl). Amplicons were purified away from reaction components using the Qiagen MinElute™ columns and quantitated as previously described.

A genomic DNA sample was prepared per standard protocol. Twenty µg of the sample with linkers attached was dried with 100 µg Cot-1 DNA and resuspended in 7.5 µl hybridization buffer (Roche NimbleGen, Madison, Wis.) and 3 µl formamide. A 1 µg aliquot of capture probes was dried and resuspended in 4.5 µl diH$_2$O. The sample solution was incubated at 95° C. for 10 min. to denature the DNA and added to the capture probe solution. The mixture was transferred to a PCR tube and placed in a thermal cycler at 42° C. for 3 days to allow duplex formation to occur.

After hybridization, the duplexes were bound to streptavidin coated paramagnetic beads (Dynal®, Invitrogen, Carlsbad, Calif.). One hundred microliters of beads were washed three times with 2× BW buffer (10 mM Tris HCl, 1 mM EDTA, 2M NaCl) and resuspended in the hybridization duplex mixture. Binding between the beads and duplexes was allowed to occur over 45 min. at 42° C. with occasional gentle mixing. Bound beads were isolated using a magnet and briefly washed in Wash Buffer I (0.2×SSC, 0.2% (v/v) SDS, 0.1 mM DTT) at room temperature, followed by two washes (each wash for 5 min. at 4 7° C.) in 200 µl Stringent Wash Buffer (0.1M MES pH 6.65, 0.1M NaCl, 0.1% Tween 20), an additional wash in Wash Buffer I for 2 min. at room temperature, once with Wash Buffer II (0.2×SSC, 0.1 mM DTT) for 1 min. at room temperature and finally for 30 sec. in Wash Buffer III (0.05×SSC, 0.1 mM DTT) at room temperature.

Captured fragments were eluted from the beads. The washed bead solution in Wash Buffer III was transferred to a 1.5 ml Eppendorf tube, the beads were isolated with a magnet, the wash buffer removed and replaced with 100 µl 95° C. diH$_2$O and the beads released from the magnet. The suspended beads were incubated at 95° C. for 5 min. after which the beads were captured and gently washed with 95° C. diH$_2$O to elute the captured fragments. The eluate was removed and the beads were washed again, for a total of three water washes; total of 10 min. with final volume of pooled eluate approximately 300 µl. After the final wash, residual magnetic beads were removed from the pooled eluate by additional magnetic capture and transfer of the eluate to a new tube. The solution was dried down and the captured, eluted fragments were resuspended in 263 µl diH$_2$O in preparation for subsequent LM-PCR. Ligation was performed by established protocols known to those skilled in the art, using a ligator of sequence 5'-CTCGAGAATTCTG-GATCC-3' (SEQ ID NO:21).

Following LM-PCR, the captured fragments were subjected to ultradeep sequencing using the 454 FLX platform (454 Life Sciences, Branford, Conn.). Alternatively, LM-PCR can be avoided by ligating 454 sequencing adaptor sequences to the pre-enrichment sample. In the latter case, the eluted enriched sequences can be added directly in the emulsion PCR of the 454 FLX platform workflow.

FIG. 2 illustrates a resequencing experiment from fragments captured in solution using the methods as described above. The qPCR controls utilizing PCR control primer sequences indicate an average of 2600 fold enrichment across the four control loci.

qPCR Control Primer Sequences:

```
                                              (SEQ ID NO: 22)
qPCR gSel-0210F GACCCTCTTACCTTGGCATTCTC (SEQ ID NO: 23)
qPCR gSel-0210R GCTGGTACCCATTGGCAACT (SEQ ID NO: 24)
qPCR gSel-0271F GGAGTGAGTGGTTTTTCTTCATTTTT (SEQ ID NO: 25)
qPCR gSel-0271R GCGCCACAAAGAGACATTCA (SEQ ID NO: 26)
qPCR gSel-0266F AAGGCCATACTTGGGTGAACTG (SEQ ID NO: 27)
qPCR gSel-0266R GCTCTGATTGGTGGCTTCGT (SEQ ID NO: 28)
qPCR gSel-0283F TGCTTGCAGGTGTCTCTCAGA (SEQ ID NO: 29)
qPCR gSel-0283R CAGTGAGATATTTGGTACCATGGTGTA
```

Indeed, conformance wherein the percentage of what is expected upon resequencing to what is realized upon resequencing is approximately 100% for almost all regions resequenced.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

Each reference identified in the present application is herein incorporated by reference in its entirety.

What is claimed is:

1. A method for isolating and reducing the complexity of a plurality of nucleic acid sequences comprising:
   (a) providing:
      (i) a solid support wherein the solid support comprises hybridization probes hybridizable to target nucleic acid sequences,
      (ii) a nucleic acid sample comprising target nucleic acid sequences,
   (b) releasing the hybridization probes from the solid support, such that the hybridization probes are in solution,
   (c) amplifying the hybridization probes in solution, wherein the amplification products comprise a binding moiety and wherein the amplification products are maintained in solution,
   (d) hybridizing the nucleic acid sample to the amplification products in solution such that hybridization between the amplification products and target nucleic acid sequences is allowed to occur, and such that target nucleic acid/amplification product hybridization complexes are formed,
   (e) separating the target nucleic acid/amplification product hybridization complexes away from non-specifically hybridized nucleic acids by the binding moiety, and
   (f) eluting the hybridized target nucleic acid sequences from the target nucleic acid/amplification product hybridization complexes, thereby isolating and reducing the complexity of a plurality of nucleic acid sequences.

2. The method according to claim 1, further comprising sequencing the eluted target nucleic acid sequences.

3. The method according to claim 1, wherein the solid support is a microarray slide.

4. The method according to claim 1, wherein the nucleic acid sample is a fragmented genomic DNA sample.

5. The method according to claim 4, wherein the fragmented genomic DNA sample further comprises adaptor molecules at one or both ends of the fragments of genomic DNA sample.

6. The method according to claim 1, wherein the hybridization probes further comprise primer binding sequences at one or both ends of the probes.

7. The method according to claim 6, wherein the primer binding sequences when present at both ends of the probes are the same.

8. The method according to claim 6, wherein the primer binding sequences when present at both ends of the probes are different.

9. The method according to claim 1, wherein the amplifying comprises exponential polymerase chain reaction.

10. The method according to claim 9, wherein the amplifying further comprises asymmetric polymerase chain reaction.

11. The method according to claim 1, wherein the binding moiety is a biotin binding moiety.

12. The method according to claim 11, wherein the separating comprises binding the biotin binding moiety to a streptavidin coated substrate.

13. The method according to claim 12, wherein the streptavidin coated substrate is a streptavidin coated paramagnetic particle.

14. The method according to claim 1, further comprising washing the separated target nucleic acid/amplification product hybridization complexes prior to elution.

15. The method according to claim 1, wherein the plurality of nucleic acid sequences contains the whole genome or at least one chromosome of an organism or at least one nucleic acid molecule with a size of at least about 200 kb.

16. The method according to claim 4, wherein the probes are selected from:
   a plurality of probes that defines a plurality of exons, introns or regulatory sequences from a plurality of genetic loci,
   a plurality of probes that defines the complete sequence of at least one single genetic locus, the locus having a size of at least 100 kb,
   a plurality of probes that defines sites known to contain single nucleotide polymorphisms (SNPs), or
   a plurality of probes that defines an array designed to capture the complete sequence of at least one complete chromosome.

17. A method for determining nucleic acid sequence information of at least one region of nucleic acid, the method comprising the steps of:
   (1) reducing the genetic complexity of a population of nucleic acid molecules according to a method according to claim 1, and
   (2) determining the nucleic acid sequence of the captured molecules, by performing sequencing by synthesis reactions.

18. A method for detecting coding region variation relative to a reference genome, the method comprising the steps of:
   (1) reducing the genetic complexity of a population of nucleic acid molecules according to a method according to claim 1,
   (2) determining the nucleic acid sequence of the captured molecules, and
   (3) comparing the determined sequence to sequences in a database of the reference genome, to sequences in a database of polymorphisms in the reference genome to identify variants from the reference genome.

* * * * *